US009512224B2

(12) United States Patent
Zauderer

(10) Patent No.: US 9,512,224 B2
(45) Date of Patent: Dec. 6, 2016

(54) USE OF SEMAPHORIN-4D BINDING MOLECULES FOR TREATMENT OF ATHEROSCLEROSIS

(71) Applicant: Vaccinex, Inc., Rochester, NY (US)

(72) Inventor: Maurice Zauderer, Pittsford, NY (US)

(73) Assignee: Vaccinex, Inc., Rochester, NY (US)

( * ) Notice: Subject to any disclaimer, the term of this patent is extended or adjusted under 35 U.S.C. 154(b) by 0 days.

(21) Appl. No.: 14/511,679

(22) Filed: Oct. 10, 2014

(65) Prior Publication Data

US 2015/0104462 A1    Apr. 16, 2015

Related U.S. Application Data

(60) Provisional application No. 61/889,421, filed on Oct. 10, 2013.

(51) Int. Cl.
| | |
|---|---|
| *A61P 9/10* | (2006.01) |
| *A61K 39/395* | (2006.01) |
| *C07K 16/28* | (2006.01) |
| *C07K 14/705* | (2006.01) |
| *A61K 39/00* | (2006.01) |

(52) U.S. Cl.
CPC ....... *C07K 16/2803* (2013.01); *A61K 39/3955* (2013.01); *A61K 2039/505* (2013.01); *C07K 14/705* (2013.01); *C07K 14/70596* (2013.01); *C07K 2317/76* (2013.01)

(58) Field of Classification Search
None
See application file for complete search history.

(56) References Cited

U.S. PATENT DOCUMENTS

| | | |
|---|---|---|
| 5,070,192 A | 12/1991 | Earnshaw et al. |
| 5,595,756 A | 1/1997 | Bally et al. |
| 6,576,754 B2 | 6/2003 | Hall et al. |
| 6,635,742 B1 | 10/2003 | Boyle et al. |
| 6,884,879 B1 | 4/2005 | Baca et al. |
| 7,060,269 B1 | 6/2006 | Baca et al. |
| 7,169,901 B2 | 1/2007 | Baca et al. |
| 7,351,803 B2 | 4/2008 | Johnson et al. |
| 7,407,766 B1 | 8/2008 | Fujisawa et al. |
| 7,414,108 B2 | 8/2008 | Laus et al. |
| 7,498,416 B2 | 3/2009 | Yayon et al. |
| 7,700,102 B2 | 4/2010 | Hall et al. |
| 7,919,246 B2 | 4/2011 | Lai et al. |
| 7,919,594 B2 | 4/2011 | Smith et al. |

(Continued)

FOREIGN PATENT DOCUMENTS

| | | |
|---|---|---|
| EP | 1442749 | 1/2003 |
| EP | 1365018 | 11/2003 |

(Continued)

OTHER PUBLICATIONS

Auerbach et al., "Angiogenesis Assays: Problems and Pitfalls", Cancer and Metastasis Reviews, pp. 167-172, vol. 19, Kluwer Academic Publishers (2000).

(Continued)

*Primary Examiner* — Zachary Howard
(74) *Attorney, Agent, or Firm* — Thompson Coburn LLP

(57) ABSTRACT

Provided herein are methods for reducing, inhibiting, suppressing and/or delaying atherosclerotic plaque growth or neovascularization in a subject having atherosclerosis, comprising administering to the subject an effective amount of an isolated binding molecule which specifically binds to Semaphorin-4D (SEMA4D) or to its high affinity Plexin-B1 receptor.

22 Claims, 3 Drawing Sheets

(56) References Cited

U.S. PATENT DOCUMENTS

Figure 1A:
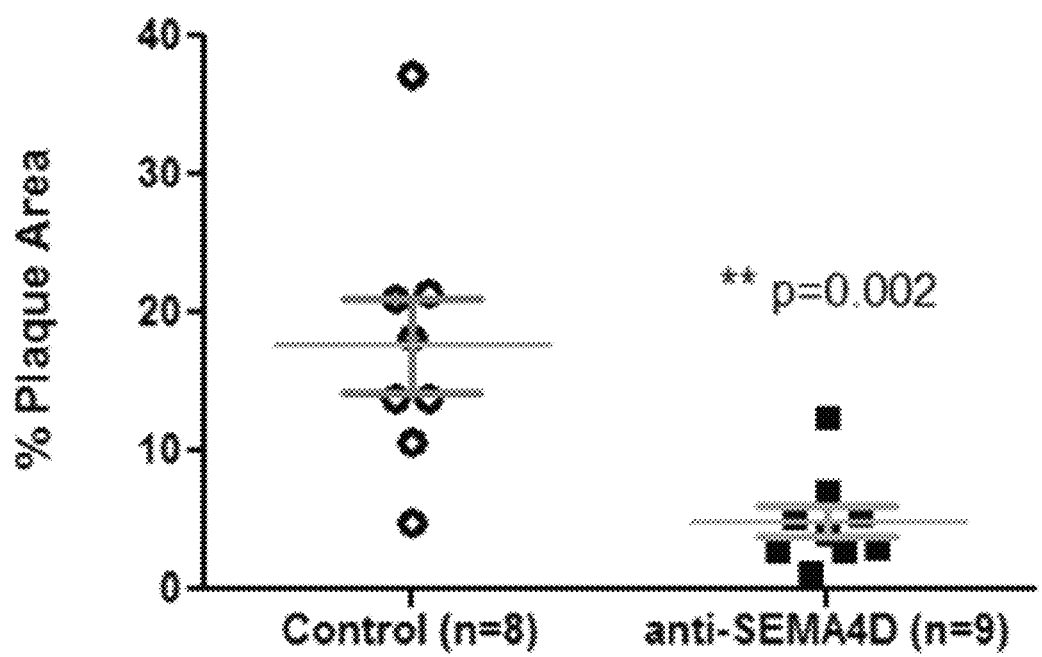

| | | | |
|---|---|---|---|
| 8,067,247 | B2 | 11/2011 | Belin et al. |
| 8,496,938 | B2 | 7/2013 | Smith et al. |
| 8,790,652 | B2 | 7/2014 | Basile et al. |
| 8,816,058 | B2 | 8/2014 | Smith et al. |
| 9,090,709 | B2 | 7/2015 | Fisher et al. |
| 9,243,068 | B2 | 1/2016 | Evans et al. |
| 9,249,227 | B2 | 2/2016 | Smith et al. |
| 2002/0037851 | A1 | 3/2002 | Fleckenstein et al. |
| 2003/0158402 | A1 | 8/2003 | Hall et al. |
| 2005/0147612 | A1 | 7/2005 | Yayon et al. |
| 2006/0147449 | A1 | 7/2006 | Brass et al. |
| 2006/0233793 | A1 | 10/2006 | Belin et al. |
| 2007/0098707 | A1 | 5/2007 | Kong-Beltran et al. |
| 2007/0148177 | A1 | 6/2007 | Fyfe et al. |
| 2009/0181035 | A1 | 7/2009 | Watts et al. |
| 2010/0040617 | A1* | 2/2010 | Brass ............... C07K 16/2803 514/1.1 |
| 2010/0285036 | A1* | 11/2010 | Smith ............... C07K 16/2803 424/172.1 |
| 2012/0027758 | A1 | 2/2012 | Belin et al. |
| 2012/0064035 | A1 | 3/2012 | Hadden et al. |
| 2012/0082663 | A1 | 4/2012 | Dennis et al. |
| 2012/0270268 | A1 | 10/2012 | Smith et al. |
| 2013/0095118 | A1 | 4/2013 | Smith et al. |
| 2013/0142810 | A1 | 6/2013 | Basile et al. |
| 2013/0274449 | A1 | 10/2013 | Smith et al. |
| 2013/0288927 | A1 | 10/2013 | Smith et al. |
| 2013/0302320 | A1 | 11/2013 | Smith et al. |
| 2014/0072578 | A1 | 3/2014 | Smith et al. |
| 2014/0099334 | A1 | 4/2014 | Fisher et al. |
| 2014/0303358 | A1 | 10/2014 | Takayanagi |
| 2015/0044219 | A1 | 2/2015 | Evans et al. |
| 2015/0104462 | A1 | 4/2015 | Zauderer |
| 2015/0110800 | A1 | 4/2015 | Smith et al. |
| 2015/0353641 | A1 | 12/2015 | Smith et al. |

FOREIGN PATENT DOCUMENTS

| | | |
|---|---|---|
| JP | 2007-308465 | 11/2007 |
| WO | 93/14125 | 7/1993 |
| WO | 95/07706 | 3/1995 |
| WO | 97/17368 | 5/1997 |
| WO | 00/28016 | 5/2000 |
| WO | 03/100041 | 12/2003 |
| WO | 2004/067034 | 8/2004 |
| WO | 2005/000900 | 1/2005 |
| WO | 2006/110594 | 10/2006 |
| WO | 2008/100995 | 8/2008 |
| WO | 2010/129917 | 11/2010 |
| WO | 2011/159704 | 12/2011 |
| WO | 2013/055922 | 4/2013 |
| WO | 2013/148854 | 10/2013 |
| WO | 2013170221 | 11/2013 |
| WO | 2014/209802 | 12/2014 |
| WO | 2015/054628 | 4/2015 |
| WO | 2015/061330 | 4/2015 |

OTHER PUBLICATIONS

Barger et al., "Hypothesis: vasa vasorum and neovascularization of Human Coronary Arteries. A Possible Role in the Pathophysiology of Atherosclerosis," New England Journal of Medicine, 310: 175-177, (1984).

Basile et al., "Semaphorin 4D Provides a Link Between Axon Guidance Processes and Tumor-Induced Angiogenesis", Proceedings of the National Academy of Sciences, pp. 9017-9022, vol. 103 No. 24, National Academy of Sciences (2006).

Basile et al., "Plexin-B1 Utilizes RhoA and Rho Kinase to Promote the Integrin-dependent Activation of Akt and Erk and Endothelial Cell Motility", Journal of Biological Chemistry, pp. 34888-34895, vol. 282 No. 48 (2007).

Basile et al., "Class IV semaphorins promote angiogenesis by stimulating Rho-initiated pathways through plexin-B," Cancer Research, vol. 64 pp. 5212-5224, Cancer Res 64: 5212-5224 (2004).

Baxter et al., "Activation Rules: The Two-Signal Theories of Immune Activation," Nature Reviews Immunology, pp. 439-446, vol. 2, No. 6 (2002).

Beam et al., "Blood, Brain, and Cerebrospinal Fluid Concentrations of Several Antibiotics in Rabbits with Intact and Inflamed Meninges," Antimicrobial Agents and Chemotherapy, pp. 710-716, vol. 12, No. 6, American Society for Microbiology, United States (1977).

Billard et al., "Switch in the Protein Tyrosine Phosphatase Associated with Human CD 100 Semaphorin at Terminal B-Cell Differentiation Stage", Blood, pp. 965-972, vol. 95 No. 3, The American Society of Hematology, United States (2000).

Bleck et al., "An Alternative Method for the Rapid Generation of Stable, High-Expressing Mammalian Cell Lines," Bioprocessing Journal, pp. 36-42, vol. 5, No. 4, International Society for BioProcess Technology, United States (2005).

Bougeret et al, "Increased Surface Expression of a Newly Identified 150-kDa Dimer Early After Human T Lymphocyte Activation" The Journal of Immunology, pp. 318-323, vol. 148 No. 2, The American Association of Immunologists, United States (1992).

Brand et al., "Collagen-Induced Arthritis", Nature Protocols, pp. 1269-1275, vol. 2 No. 5, Nature Publishing Group, England (2007).

Brown et al., "Tolerance to Single, but Not Multiple, Amino Acid Replacements in Antibody VH CDR2: A Means of Minimizing B Cell Wastage from Somatic Hypermutation?", Journal of Immunology, pp. 3285-3291 at 3290 and Tables 1 and 2, vol. 156 No. 9, The American Association of Immunologists (1996).

Burgess et al., "Possible Dissociation of the Heparin-Binding and Mitogenic Activities of Heparin-Binding (Acidic Fibroblast) Growth Factor-1 From Its Receptor-Binding Activities by Site-Directed Mutagenesis of a Single Lysine Residue", The Journal of Cell Biology pp. 2129-2138, The Rockefeller University Press, United States (1990).

Bussolino et al., "Molecular Mechanisms of Blood Vessel Formation," Trends in Biochemical Sciences, pp. 251-256, vol. 22 No. 7, Elsevier Trends Journals, England (1997).

Campos et al., "Ki-67 and CD 100 Immunohistochemical Expression is Associated with Local Recurrance and Poor Prognosis in Soft Tissue Sarcomas, Respectively", Oncology Letters, pp. 1527-1535, vol. 5 (2013).

Carmeliet, "Angiogenesis in health and disease," Nature Medicine, pp. 653-660, vol. 9 No. 6, Nature Publishing Company, United States (2003).

Chabbert-De Ponnat et al., "Soluble CD100 Functions on Human Monocytes and Immature Dendritic Cells Require Plexin C1 and Plexin B1, Respectively", International Immunology, pp. 439-447, vol. 4, Oxford University Press, England (2005).

Chen et al., "Generation and Analysis of Random Point Mutations in an Antibody CDR2 Sequence: Many Mutated Antibodies Lose their Ability to Bind Antigen," Journal of Experimental Medicine, pp. 855-866, vol. 176 (1992).

Cheng et al., "Angiotensin Type 1 Receptor Blocker Reduces Intimal Neovascularization and Plaque Growth in Apolipoprotein E-deficient Mice," Hypertension vol. 57, pp. 981-989 (2011).

Ch'Ng et al., "Prognostic Significance of CD100 Expression in Soft Tissue Progression", Cancer, pp. 164-172, vol. 110, Issue 3 (2007).

Claesson-Welsh, "Novel paths to blood vessel formation," Blood 105(11):4153-4154, The American Society of Hematology, United States (2005).

Clark et al., "Discovery and Development of Janus Kinase (JAK) Inhibitors for Inflammatory Diseases", Journal of Medicinal Chemistry, pp. 5023-5038, Vol. 57, American Chemical Society (2014).

Colman et al., "Effects of Amino Acid Sequence Changes on Antibody-Antigen Interactions," Research in Immunology, pp. 33-36, vol. 145 (1994).

Conrotto et al., "Sema4D Induces Angiogenesis Through Met Recruitment by Plexin B1," Blood, pp. 4321-4329, vol. 105 No. 11, The American Society of Hematology, United States (2005).

(56) References Cited

OTHER PUBLICATIONS

Cornelius et al., "Abstract 936: Nonclinical Safety and Pharmacology of VX15/2503: a Humanized IgG4 Monoclonal Antibody to SEMA4D", Cancer Research (2012), retrieved from http://cancerres,aacrjournals.org/content/72/8_Supplement/936.short on Sep. 25, 2015, the whole document.
Curran et al., "Systemic 4-1BB Activation Induces a Novel T cell Phenotype Driven by High Expression of Eomesodermin," The Journal of Experimental Medicine, pp. 743-755, vol. 210 (2013).
Database GenBank, Apr. 18, 2005, Adams, "M.Musculus mRNA for Semaphorin B", Data Accession No. X85991.
Database GenBank, Apr. 24, 1997, Hillier et al., "zt85a06.r1", Data Accession No. AA394007.
Database GenBank, Jan. 31, 1997, Strausberg, "zs16g08.r1", Data Accession No. AA262446.
De Pascalis et al., "Grafting of 'Abbreviated' Complementarity-Determining Regions Containing Specificity-Determining Residues Essential for Ligand Contact to Engineer a Less Immunogenic Humanized Monoclonal Antibody," Journal of Immunology, pp. 3076-3084, vol. 169 No. 6 (2002).
Delaire et al., "Biological Activity of Soluble CD100. II. Soluble CD100, Similarly to H-Sema III, Inhibits Immune Cell Migration", The Journal of Immunology, pp. 4348-4354, vol. 166, The American Association of Immunologists, United States (2001).
Delaire et al., "Inhibition of Immune Cell Migration by Soluble CD100 and H-Sema III Semaphorins," Tissue Antigens, pp. 103, vol. 55 No. 1, Wiley-Blackwell, England (Abstract Only) (2000).
Dougher et al., "Autophosphorylation of KDR in the Kinase Domain is Required for Maximal VEGF-Stimulated Kinase Activity and Receptor Internalization," Oncogene, pp. 1619-1627, vol. 18 No. 8, Nature Publishing Group, England (1999).
Drake et al.,"Mechanisms of Immune Evasion by Tumors," Advances in Immunology, pp. 51-81, vol. 90 (2006).
Duran-Struuck et al., "A Novel Role for the Semaphorin Sema4D in the Induction of Allo-Responses," Biological Blood Marrow Transplant, pp. 1294-1303, vol. 13, No. 11 (2007).
Elhabazi et al., "Biological Activity of Soluble CD100. I. The Extracellular Region of CD100 is Released from the Surface of T Lymphocytes by Regulated Proteolysis," The Journal of Immunology, pp. 4341-4347, vol. 166, The American Association of Immunologists, United States (2001).
Elhabazi et al., "Structure and Function of the Immune Semaphorin CD100/SEMA4D," Critical Review in Immunology, pp. 65-81, vol. 23 No. 1-2, Begell House, Inc. United States (2003).
Elhabazi et al., "The Human Semaphorin-Like Leukocyte Cell Surface Molecule CD100 Associates with a Serine Kinase Activity", The Journal of Biological Chemistry, pp. 23515-23520, vol. 272 No. 38, The American Society for Biochemistry and Molecular Biology, Inc., United States (1997).
Ferrara, "VEGF and the Quest for Tumour Angiogenesis Factors," Nature Reviews Cancer, pp. 795-803, vol. 2 No. 10, Nature Publishing Group, England (2002).
Furuyama et al., "Identification of a Novel Transmembrane Semaphorin Expressed on Lymphocytes", Journal of Biological Chemistry, pp. 33376-33381, vol. 271 No. 52 (1996).
Gauld et al., "B Cell Antigen Receptor Signaling: Roles in Cell Development and Disease," Science, pp. 1641-1642, vol. 296, The American Association for the Advancement of Science, Untied States (2002).
Giordano et al., "The Semaphorin 4D Receptor Controls Invasive Growth by Coupling with Met," Nature Cell Biology, Sep. 2002, pp. 720-724, vol. 4 No. 9, Nature Publishing Group, England.
Goldsby et al., "Autoimmunity", Kuby Immunology, pp. 502-504, vol. 4, W.H. Freeman and Company, United States (2000).
Gursoy-Ozdemir et al., "Microvascular Protection is Essential for Successful Neuroprotection in Stroke", Journal of Neurochemistry, pp. 2-11, vol. 123 Suppl. 2 (2012).
Hajj-Ali et al., "Primary Angiitis of the Central Nervous System," Autoimmunity Reviews, pp. 463-466, vol. 12 (2013).

Hall et al., "Human CD100, A Novel Leukocyte Semaphorin That Promotes B-Cell Aggregation and Differentiation", Proceeding of the National Academy of Sciences, pp. 11780-11785, vol. 93, National Academy of Sciences (1996).
Hebert et al., "The Molecular Dating Game: An Antibody Heavy Chain Hangs Loose with a Chaperone while Waiting for Its Life Partner", Molecular Cell, pp. 635-636, vol. 34 No. 6, Cell Press, United States (2009).
Herold et al., "Activation Signals Are Delivered Through Two Distinct Epitopes of CD100, A Unique 150 kDa Human Lymphocyte Surface Structure Previously Defined by BB18 mAb", International Immunology, pp. 1-8, vol. 7 No. 1, Oxford University Press, England (1994).
Herold, C., et al., "CD100 defines a newly identified 150-kDa human lymphocyte surface structure;" T-cell antigens—papers T1:50-51 (1994).
Hicklin et al., "Role of the Vascular Endothelial Growth Factor Pathway in Tumor Growth and Angiogenesis," Journal of Clinical Oncology, pp. 1011-1027, vol. 23 No. 5, American Society of Clinical Oncology, United States (2005).
Ishida et al., "Involvement of CD100, A Lymphocyte Semaphorin, in the Activation of the Human Immune System Via CD72: Implications for the Regulation of Immune and Inflammatory Responses", International Immunology, pp. 17-23, vol. 15 No. 8, Oxford University Press, England (2003).
Iwahashi et al., "CDR Substitutions of a Humanized Monoclonal Antibody (CC49): Contributions of Individual CDRs to Antigen Binding and Immunogenicity," Molecular Immunology, pp. 1079-1091, vol. 36 (1999).
Janssen et al., "Structural basis of semaphorin-plexin signaling," Nature, pp. 1118-1122, vol. 467, Nature Publishing Group, England (2010).
Jenkins et al., "Antigen Presentation by Chemically Modified Splenocytes Induces Antigen-Specific T Cell Unresponsiveness in Vitro and in Vivo," Journal of Experimental Medicine, pp. 302-319, vol. 165 No. 2 (1987).
Jonason at al., "Development of an anti-SEMA4D monoclonal antibody for the treatment of Multiple Sclerosis", 5th Joint Triennial Congress of the European and Americas Committees for Treatment and Research in Multiple Sclerosis, Amsterdam, The Netherlands (2011).
Jonsson-Rylander et al., "Role of ADAMTS-1 in Atherosclerosis Remodeling of Carotid Artery, Immunohistochemistry, and Proteolysis of Versican," Arteriosclerosis Thrombosis, and Vascular Biology, vol. 25, pp. 180-185 (2005).
Kang et al., "Semaphorins in bone development, homeostasis, and disease," Seminars in Cell & Dev Biol vol. 24, pp. 163-171 (2013).
Kikutani et al., "Semaphorins in Interactions Between T Cells and Antigen-Presenting Cells", Nature Reviews Immunology, pp. 159-167, vol. 3, Nature Publishing Group, United States (2003).
Kim et al., "Inhibition of vascular endothelial growth factor-induced angiogenesis suppresses tumour growth in vivo," Nature, pp. 841-844, vol. 362, No. 6423, Nature Publishing Group, England (1993).
Kolodgie et al., "Intraplaque Hemorrhage and Progression of Coronary Atheroma," New England Journal of Medicine, vol. 349, pp. 2316-2325 (2003).
Kornbluth et al., "Novel Tyrosine Kinase Identified by Phosphotyrosine Antibody Screening of cDNA Libraries", Molecular and Cellular Biology, pp. 5541-5544, vol. 8 No. 12, American Society for Microbiology, United States (1988).
Kruger et al., "Semaphorins Command Cells to Move", Nature Reviews Molecular Cell Biology, pp. 789-800, vol. 6, Nature Publishing Group, London (2005).
Kumamoto et al., "Intimal neovascularization in human coronary atherosclerosis: Its origin and pathophysiological significance," Hum Pathol 26: 450-456 (1995).
Kumanogoh et al., "Identification of CD72 as a Lymphocyte Receptor for the Class IV Semaphorin CD100: A Novel Mechanism for Regulating B Cell Signaling", Immunity, pp. 621-631, vol. 13, No. 5, Cell Press, Cambridge, Massachusetts (2000).
Kumanogoh et al., "Immune Semaphorins: A New Area of Semaphorin Research", Journal of Cell Science, pp. 3463-3470, vol. 116, The Company of Biologists Ltd., United Kingdom (2003).

(56) References Cited

OTHER PUBLICATIONS

Kumanogoh et al., "Requirement for CD100-CD72 Interaction in Fine-Tuning of B-Cell Antigen Receptor Signaling and Homeostatic Maintenance of the B-Cell Compartment", International Immunology, pp. 1277-1282, vol. 17 No. 10, The Japanese Society for Immunology, Oxford University Press, England (2005).
Kumanogoh et al., "Requirement for the Lymphocyte Semaphorin CD100, in the Induction of Antigen-Specific T Cells and the Maturation of Dendritic Cells", Journal of Immunology, pp. 1175-1181, The American Association of Immunologists, United States (2002).
Kumanogoh et al., "The CD100-CD72 Interaction: A Novel Mechanism of Immune Regulation" Trends in Immunology, pp. 670-676, vol. 22, No. 12, Elsevier Science Ltd., United States (2011).
Lafferty et al., "A New Analysis of Allogeneic Interactions," Australian Journal Experimental Biology and Medical Science, pp. 27-42, vol. 53, No. 1 (1975).
Li et al., "CD72 Down-Modulates BCR-Induced Signal Transduction and Diminishes Survival in Primary Mature B Lymphocytes," The Journal of Immunology, pp. 5321-5328, vol. 176, The American Association of Immunologists, United States (2006).
Li et al., "Modulation of Peripheral B Cell Tolerance by CD72 in a Murine Model," Arthritis and Rheumatism, pp. 3192-3904, vol. 58 No. 10, The American College of Rheumatology, United States (2008).
Love et al., "The ligand-binding face of the semaphorins revealed by the high-resolution crystal structure of SEMA4D," Nature Structural and Molecular Biology, pp. 843-848, vol. 10, Nature Pub. Co., United States (2003).
Lutgens et al., "Requirement for CD154 in the Progression of Atherosclerosis," Nat Med, vol. 11, pp. 1313-1316 (1999).
Mach et al., "Functional CD40 ligand is expressed on human vascular endothelial cells, smooth muscle cells, and macrophages: Implications for CD40-CD40 ligand signaling in atherosclerosis," Proceedings of the National Academy of Sciences USA, vol. 94, pp. 1931-1936 (1997).
Mach et al., Reduction of atherosclerosis in mice by inhibition of CD40 signalling, Nature, vol. 394, pp. 200-203 (1998).
Mach et al., "Activation of Monocyte/Macrophage Functions Related to Acute Atheroma Complication by Ligation of CD40," Circulation, vol. 96, pp. 396-399 (1997).
Mizrahi et al., "CD100 on NK Cells Enhance IFN[gamma] Secretion and Killing of Target Cells Expressing CD72," PLOS One, pp. e818, vol. 2, No. 9, New York University School of Medicine, United States (2007).
Moreno et al., "Neovascularization in Human Atherosclerosis," Circulation, vol. 113, pp. 2245-2252 (2006).
Moulton et al., Angiogenesis inhibitors endostatin or TNP-470 reduce intimal neovascularization and plaque growth in apolipoprotein E-deficient mice, Circulation vol. 99, pp. 1726-1732 (1999).
Moulton et al., Inhibition of plaque neovascularization reduces macrophage accumulation and progression of advanced atherosclerosis, Proceedings of the National Academy of Sciences USA 100: 4736-4741 (2003).
Nelson, "Antibody Fragments", Landes Bioscience, pp. 77-83, vol. 2, Issue 1 (2009).
O'Brien et al., "Angiogenesis in Human Coronary Atherosclerotic Plaques," American Journal of Pathology, vol. 145, pp. 883-894 (1994).
Oinuma et al., "Semaphorin 4D/Plexin-B1-Mediated R-Ras GAP Activity Inhibits Cell Migration by Regulating beta-1 Integrin Activity," The Journal of Cell Biology, pp. 601-613, vol. 173 No. 801 (2006).
Pasterkamp et al., "R-Ras fills another GAP in Semaphorin Signalling," Trends in Cell Biology, pp. 61-64, vol. 15 No. 2, Elsevier Science Publishers, England (2005).
Pasterkamp, Getting Neural Circuits into Shape with Semaphorins, Nat Rev Neurosci. vol. 13, pp. 605-618 (2012).

Patnaik et al., "Safety, Pharmacokinetics, and Pharmacodynamics of a Humanized Anti-Semaphorin 4D Antibody, in a First-In-Human Study of Patients with Advanced Solid Tumors," Clinical Cancer Research, pp. 1-10 (2015).
Peranzoni et al., "Positive and Negative Influence of the Matrix Architecture on Antitumor Immune Surveillance," Cellular and Molecular Life Science, pp. 4431-4448, vol. 70 (2013).
Regev et al., "Semaphorin-4D (Sema-4D), the Plexin-B1 Ligand, is Involved in Mouse Ovary Follicular Development," Reproductive Biology and Endocrinology, vol. 5, Issue 12, 8 pages (2007).
Risau, "Mechanisms of Angiogenesis," Nature, pp. 671-674, vol. 386, No. 6626, Nature Publishing Group, England (1997).
Roth et al., "The Many Faces of Semaphorins: From Development to Pathology," CMLS Cellular and Molecular Life Sciences, pp. 649-666, vol. 66 No. 4 (2008).
Rudikoff et al., "Single Amino Acid Substitution Altering Antigen-Binding Specificity," Proc. Natl. Acad. Sci. USA, pp. 1979-1983, vol. 79, No. 6 (1982).
Shi et al., "The Class IV Semaphorin CD100 Plays Nonredundant Roles in the Immune System: Defective B and T Cell Activation in CD100-Deficient Mice," Immunity, pp. 633-642, vol. 13, Cell Press, United States (2000).
Sierra et al., "Tumor Angiogenesis and Progression are Enhanced by Sema4D Produced by Tumor-Associated Macrophages", Journal of Experimental Medicine, pp. 1673-1685, vol. 205 No. 7, The Rockefeller University Press, United States (2008).
Suzuki et al., "Semaphorins and Their Receptors in Immune Cell Interactions," Nature Immunology, pp. 17-23, vol. 9 No. 1 (2008).
Takeuchi et al., "Angiogenesis in Primary Central Nervous System Lymphoma (PCNSL)," Journal of Neuro-Oncology, pp. 141-145, vol. 84 (2007).
Tamagnone et al., "Plexins are a Large Family of Receptors for Transmembrane, Secreted, and GPI-Anchored Semaphorins in Vertebrates", Cell, pp. 71-80, vol. 99, No. 1, Cell Press, United States (1999).
Tardif et al., Imaging Biomarkers in Atherosclerosis Trials, Circ. Cardiovasc Imaging, pp. 319-333 (2011).
Turner et al., "Plexin-Induced Collapse Assay in COS Cells", Methods in Enzymology, pp. 665-676, vol. 406, Elsevier Inc., United States (2006).
Unverified, machine-generated English Language translation of the French Patent Publication No. FR 2686087 A1 (corresponds to International Patent Application No. WO 93/14125 A1), European Patent Office, espacenet database—Worldwide (1993).
Van Lammeren et al., "Atherosclerotic Plaque Biomarkers: Beyond the Horizon of the Vulnerable Plaque," Current Cardiology Reviews, vol. 7, pp. 22-27 (2011).
Virmani et al, "Lessons from Sudden Coronary Death," Arteriosclerosis Thrombosis and Vascular Biology, vol. 20, No. 5, pp. 1262-1275 (2000).
Wang et al., "Functional Soluble CD100/Sema4D Released from Activated Lymphocytes: Possible Role in Normal and Pathologic Immune Responses", Blood, pp. 3498-3504, vol. 97, No. 11, The American Society of Hematology, United States (2001).
Watanabe et al., "Enhanced Immune Response in Transgenic Mice Expressing a Truncated Form of the Lymphocyte Semaphorin CD100," The Journal of Immunology, pp. 4321-4328, The American Association of Immunologists, United States (2001).
Waubant, "Biomarkers indicative of blood-brain barrier disruption in multiple sclerosis," Disease Markers, pp. 235-244, vol. 22, IOS Press (2006).
Westin et al., "Endothelial Proliferation and Increased Blood-Brain Barrier Permeability in the Basal Ganglia in a Rat Model of 3,4-Dihydroxyphenyl-L-Alanine-Induced Dyskinesia," The Journal of Neuroscience, pp. 9448-9461, vol. 26, No. 37, Society for Neuroscience, United States (2006).
Witherden et al., "The CD100 Receptor Interacts with Its Plexin B2 Ligand to Regulate Epidermal gs T Cell Function," Immunity, pp. 314-325, vol. 37 No. 2, Cell Press, United States (2012).
Wu et al., "Humanization of a Murine Monoclonal Antibody by Simultaneous Optimization of Framework and CDR Residues", Journal of Molecular Biology, pp. 151-162, vol. 294 (1999).

(56) References Cited

OTHER PUBLICATIONS

Wu, "Simultaneous Humanization and Affinity Optimization of Monoclonal Antibodies", Methods in Molecular Biology, pp. 197-212, vol. 207, Humana Press, Inc., New Jersey, United States (2003).

Xiao-Guang et al., "Preparation and Identification of Monoclonal Antibodies Against CD100 Molecule", Chinese Journal of Cellular and Molecular Immunology, pp. 80-82, vol. 19 No. 1, Abstract (2013).

Yukawa et al., "Deletion of Sema4D gene reduces intimal neovascularization and plaque growth in apolipoprotein E-deficient mice," International Journalof Molecular Medicine vol. 26, pp. 39-44 (2010).

Zhang et al., "Sema 4D/CD100-plexin B is a Multifunctional Counter-Receptor," Cellular and Molecular Immunology, pp. 97-98, vol. 10 (2013).

Zhang et al., Immunohistochemical study of intimal microvessels in coronary atherosclerosis, Am J Pathol 143: 164-172 (1993).

Zlokovic, "Neurovascular Pathways to Neurodegeneration in Alzheimer's Disease and other Disorders", Nature Reviews-Neuroscience, pp. 723-738, vol. 12 (2011).

Basile et al., Semaphorin 4D/Plexin-B1 Induces Endothelial Cell Migration through the Activation of PYK2, Src, and the Phosphatidylinositol 3-Kinase-Akt Pathway Mollecular and Celular Biology 25: 6889-6898 (2005).

* cited by examiner

SEQUENCE LISTING

```
<160> NUMBER OF SEQ ID NOS: 48

<210> SEQ ID NO 1
<211> LENGTH: 862
<212> TYPE: PRT
<213> ORGANISM: Homo sapiens

<400> SEQUENCE: 1

Met Arg Met Cys Thr Pro Ile Arg Gly Leu Leu Met Ala Leu Ala Val
1               5                   10                  15

Met Phe Gly Thr Ala Met Ala Phe Ala Pro Ile Pro Arg Ile Thr Trp
            20                  25                  30

Glu His Arg Glu Val His Leu Val Gln Phe His Glu Pro Asp Ile Tyr
        35                  40                  45

Asn Tyr Ser Ala Leu Leu Leu Ser Glu Asp Lys Asp Thr Leu Tyr Ile
    50                  55                  60

Gly Ala Arg Glu Ala Val Phe Ala Val Asn Ala Leu Asn Ile Ser Glu
65                  70                  75                  80
```

-continued

```
Lys Gln His Glu Val Tyr Trp Lys Val Ser Glu Asp Lys Lys Ala Lys
                85                  90                  95

Cys Ala Glu Lys Gly Lys Ser Lys Gln Thr Glu Cys Leu Asn Tyr Ile
            100                 105                 110

Arg Val Leu Gln Pro Leu Ser Ala Thr Ser Leu Tyr Val Cys Gly Thr
        115                 120                 125

Asn Ala Phe Gln Pro Ala Cys Asp His Leu Asn Leu Thr Ser Phe Lys
130                 135                 140

Phe Leu Gly Lys Asn Glu Asp Gly Lys Gly Arg Cys Pro Phe Asp Pro
145                 150                 155                 160

Ala His Ser Tyr Thr Ser Val Met Val Asp Gly Glu Leu Tyr Ser Gly
                165                 170                 175

Thr Ser Tyr Asn Phe Leu Gly Ser Glu Pro Ile Ile Ser Arg Asn Ser
            180                 185                 190

Ser His Ser Pro Leu Arg Thr Glu Tyr Ala Ile Pro Trp Leu Asn Glu
        195                 200                 205

Pro Ser Phe Val Phe Ala Asp Val Ile Arg Lys Ser Pro Asp Ser Pro
    210                 215                 220

Asp Gly Glu Asp Asp Arg Val Tyr Phe Phe Thr Glu Val Ser Val
225                 230                 235                 240

Glu Tyr Glu Phe Val Phe Arg Val Leu Ile Pro Arg Ile Ala Arg Val
                245                 250                 255

Cys Lys Gly Asp Gln Gly Gly Leu Arg Thr Leu Gln Lys Lys Trp Thr
            260                 265                 270

Ser Phe Leu Lys Ala Arg Leu Ile Cys Ser Arg Pro Asp Ser Gly Leu
        275                 280                 285

Val Phe Asn Val Leu Arg Asp Val Phe Val Leu Arg Ser Pro Gly Leu
    290                 295                 300

Lys Val Pro Val Phe Tyr Ala Leu Phe Thr Pro Gln Leu Asn Asn Val
305                 310                 315                 320

Gly Leu Ser Ala Val Cys Ala Tyr Asn Leu Ser Thr Ala Glu Glu Val
                325                 330                 335

Phe Ser His Gly Lys Tyr Met Gln Ser Thr Thr Val Glu Gln Ser His
            340                 345                 350

Thr Lys Trp Val Arg Tyr Asn Gly Pro Val Pro Lys Pro Arg Pro Gly
        355                 360                 365

Ala Cys Ile Asp Ser Glu Ala Arg Ala Ala Asn Tyr Thr Ser Ser Leu
    370                 375                 380

Asn Leu Pro Asp Lys Thr Leu Gln Phe Val Lys Asp His Pro Leu Met
385                 390                 395                 400

Asp Asp Ser Val Thr Pro Ile Asp Asn Arg Pro Arg Leu Ile Lys Lys
                405                 410                 415

Asp Val Asn Tyr Thr Gln Ile Val Val Asp Arg Thr Gln Ala Leu Asp
            420                 425                 430

Gly Thr Val Tyr Asp Val Met Phe Val Ser Thr Asp Arg Gly Ala Leu
        435                 440                 445

His Lys Ala Ile Ser Leu Glu His Ala Val His Ile Ile Glu Glu Thr
    450                 455                 460

Gln Leu Phe Gln Asp Phe Glu Pro Val Gln Thr Leu Leu Leu Ser Ser
465                 470                 475                 480

Lys Lys Gly Asn Arg Phe Val Tyr Ala Gly Ser Asn Ser Gly Val Val
                485                 490                 495

Gln Ala Pro Leu Ala Phe Cys Gly Lys His Gly Thr Cys Glu Asp Cys
```

```
                   500                 505                 510
Val Leu Ala Arg Asp Pro Tyr Cys Ala Trp Ser Pro Thr Ala Thr
            515                 520                 525

Cys Val Ala Leu His Gln Thr Glu Ser Pro Ser Arg Gly Leu Ile Gln
            530                 535                 540

Glu Met Ser Gly Asp Ala Ser Val Cys Pro Asp Lys Ser Lys Gly Ser
545                 550                 555                 560

Tyr Arg Gln His Phe Phe Lys His Gly Gly Thr Ala Glu Leu Lys Cys
            565                 570                 575

Ser Gln Lys Ser Asn Leu Ala Arg Val Phe Trp Lys Phe Gln Asn Gly
            580                 585                 590

Val Leu Lys Ala Glu Ser Pro Lys Tyr Gly Leu Met Gly Arg Lys Asn
            595                 600                 605

Leu Leu Ile Phe Asn Leu Ser Glu Gly Asp Ser Gly Val Tyr Gln Cys
            610                 615                 620

Leu Ser Glu Glu Arg Val Lys Asn Lys Thr Val Phe Gln Val Val Ala
625                 630                 635                 640

Lys His Val Leu Glu Val Lys Val Val Pro Lys Pro Val Val Ala Pro
            645                 650                 655

Thr Leu Ser Val Val Gln Thr Glu Gly Ser Arg Ile Ala Thr Lys Val
            660                 665                 670

Leu Val Ala Ser Thr Gln Gly Ser Ser Pro Pro Thr Pro Ala Val Gln
            675                 680                 685

Ala Thr Ser Ser Gly Ala Ile Thr Leu Pro Pro Lys Pro Ala Pro Thr
            690                 695                 700

Gly Thr Ser Cys Glu Pro Lys Ile Val Ile Asn Thr Val Pro Gln Leu
705                 710                 715                 720

His Ser Glu Lys Thr Met Tyr Leu Lys Ser Ser Asp Asn Arg Leu Leu
            725                 730                 735

Met Ser Leu Phe Leu Phe Phe Phe Val Leu Phe Leu Cys Leu Phe Phe
            740                 745                 750

Tyr Asn Cys Tyr Lys Gly Tyr Leu Pro Arg Gln Cys Leu Lys Phe Arg
            755                 760                 765

Ser Ala Leu Leu Ile Gly Lys Lys Pro Lys Ser Asp Phe Cys Asp
            770                 775                 780

Arg Glu Gln Ser Leu Lys Glu Thr Leu Val Glu Pro Gly Ser Phe Ser
785                 790                 795                 800

Gln Gln Asn Gly Glu His Pro Lys Pro Ala Leu Asp Thr Gly Tyr Glu
            805                 810                 815

Thr Glu Gln Asp Thr Ile Thr Ser Lys Val Pro Thr Asp Arg Glu Asp
            820                 825                 830

Ser Gln Arg Ile Asp Asp Leu Ser Ala Arg Asp Lys Pro Phe Asp Val
            835                 840                 845

Lys Cys Glu Leu Lys Phe Ala Asp Ser Asp Ala Asp Gly Asp
850                 855                 860

<210> SEQ ID NO 2
<211> LENGTH: 861
<212> TYPE: PRT
<213> ORGANISM: Murine sp.

<400> SEQUENCE: 2

Met Arg Met Cys Ala Pro Val Arg Gly Leu Phe Leu Ala Leu Val Val
1               5                   10                  15
```

-continued

```
Val Leu Arg Thr Ala Val Ala Phe Ala Pro Val Pro Arg Leu Thr Trp
             20                  25                  30
Glu His Gly Glu Val Gly Leu Val Gln Phe His Lys Pro Gly Ile Phe
         35                  40                  45
Asn Tyr Ser Ala Leu Leu Met Ser Glu Asp Lys Asp Thr Leu Tyr Val
     50                  55                  60
Gly Ala Arg Glu Ala Val Phe Ala Val Asn Ala Leu Asn Ile Ser Glu
 65                  70                  75                  80
Lys Gln His Glu Val Tyr Trp Lys Val Ser Asp Lys Lys Ser Lys
                 85                  90                  95
Cys Ala Glu Lys Gly Lys Ser Lys Gln Thr Glu Cys Leu Asn Tyr Ile
                100                 105                 110
Arg Val Leu Gln Pro Leu Ser Thr Ser Leu Tyr Val Cys Gly Thr
             115                 120                 125
Asn Ala Phe Gln Pro Thr Cys Asp His Leu Asn Leu Thr Ser Phe Lys
         130                 135                 140
Phe Leu Gly Lys Ser Glu Asp Gly Lys Gly Arg Cys Pro Phe Asp Pro
145                 150                 155                 160
Ala His Ser Tyr Thr Ser Val Met Val Gly Gly Glu Leu Tyr Ser Gly
                 165                 170                 175
Thr Ser Tyr Asn Phe Leu Gly Ser Glu Pro Ile Ile Ser Arg Asn Ser
             180                 185                 190
Ser His Ser Pro Leu Arg Thr Glu Tyr Ala Ile Pro Trp Leu Asn Glu
         195                 200                 205
Pro Ser Phe Val Phe Ala Asp Val Ile Gln Lys Ser Pro Asp Gly Pro
210                 215                 220
Glu Gly Glu Asp Asp Lys Val Tyr Phe Phe Thr Glu Val Ser Val
225                 230                 235                 240
Glu Tyr Glu Phe Val Phe Lys Leu Met Ile Pro Arg Val Ala Arg Val
                 245                 250                 255
Cys Lys Gly Asp Gln Gly Gly Leu Arg Thr Leu Gln Lys Lys Trp Thr
             260                 265                 270
Ser Phe Leu Lys Ala Arg Leu Ile Cys Ser Lys Pro Asp Ser Gly Leu
         275                 280                 285
Val Phe Asn Ile Leu Gln Asp Val Phe Val Leu Arg Ala Pro Gly Leu
290                 295                 300
Lys Glu Pro Val Phe Tyr Ala Val Phe Thr Pro Gln Leu Asn Asn Val
305                 310                 315                 320
Gly Leu Ser Ala Val Cys Ala Tyr Thr Leu Ala Thr Val Glu Ala Val
                 325                 330                 335
Phe Ser Arg Gly Lys Tyr Met Gln Ser Ala Thr Val Glu Gln Ser His
             340                 345                 350
Thr Lys Trp Val Arg Tyr Asn Gly Pro Val Pro Thr Pro Arg Pro Gly
         355                 360                 365
Ala Cys Ile Asp Ser Glu Ala Arg Ala Ala Asn Tyr Thr Ser Ser Leu
     370                 375                 380
Asn Leu Pro Asp Lys Thr Leu Gln Phe Val Lys Asp His Pro Leu Met
385                 390                 395                 400
Asp Asp Ser Val Thr Pro Ile Asp Asn Arg Pro Lys Leu Ile Lys Lys
                 405                 410                 415
Asp Val Asn Tyr Thr Gln Ile Val Val Asp Arg Thr Gln Ala Leu Asp
             420                 425                 430
Gly Thr Phe Tyr Asp Val Met Phe Ile Ser Thr Asp Arg Gly Ala Leu
```

-continued

```
            435                 440                 445
His Lys Ala Val Ile Leu Thr Lys Glu Val His Val Ile Glu Glu Thr
        450                 455                 460
Gln Leu Phe Arg Asp Ser Glu Pro Val Leu Thr Leu Leu Ser Ser
465                 470                 475                 480
Lys Lys Gly Arg Lys Phe Val Tyr Ala Gly Ser Asn Ser Gly Val Val
                485                 490                 495
Gln Ala Pro Leu Ala Phe Cys Glu Lys His Gly Ser Cys Glu Asp Cys
            500                 505                 510
Val Leu Ala Arg Asp Pro Tyr Cys Ala Trp Ser Pro Ala Ile Lys Ala
            515                 520                 525
Cys Val Thr Leu His Gln Glu Glu Ala Ser Ser Arg Gly Trp Ile Gln
        530                 535                 540
Asp Met Ser Gly Asp Thr Ser Ser Cys Leu Asp Lys Ser Lys Glu Ser
545                 550                 555                 560
Phe Asn Gln His Phe Phe Lys His Gly Gly Thr Ala Glu Leu Lys Cys
                565                 570                 575
Phe Gln Lys Ser Asn Leu Ala Arg Val Val Trp Lys Phe Gln Asn Gly
            580                 585                 590
Glu Leu Lys Ala Ala Ser Pro Lys Tyr Gly Phe Val Gly Arg Lys His
        595                 600                 605
Leu Leu Ile Phe Asn Leu Ser Asp Gly Asp Ser Gly Val Tyr Gln Cys
        610                 615                 620
Leu Ser Glu Glu Arg Val Arg Asn Lys Thr Val Ser Gln Leu Leu Ala
625                 630                 635                 640
Lys His Val Leu Glu Val Lys Met Val Pro Arg Thr Pro Ser Pro
                645                 650                 655
Thr Ser Glu Asp Ala Gln Thr Glu Gly Ser Lys Ile Thr Ser Lys Met
            660                 665                 670
Pro Val Ala Ser Thr Gln Gly Ser Ser Pro Thr Pro Ala Leu Trp
            675                 680                 685
Ala Thr Ser Pro Arg Ala Ala Thr Leu Pro Pro Lys Ser Ser Ser Gly
        690                 695                 700
Thr Ser Cys Glu Pro Lys Met Val Ile Asn Thr Val Pro Gln Leu His
705                 710                 715                 720
Ser Glu Lys Thr Val Tyr Leu Lys Ser Ser Asp Asn Arg Leu Leu Met
                725                 730                 735
Ser Leu Leu Leu Phe Ile Phe Val Leu Phe Leu Cys Leu Phe Ser Tyr
            740                 745                 750
Asn Cys Tyr Lys Gly Tyr Leu Pro Gly Gln Cys Leu Lys Phe Arg Ser
        755                 760                 765
Ala Leu Leu Gly Lys Lys Thr Pro Lys Ser Asp Phe Ser Asp Leu
        770                 775                 780
Glu Gln Ser Val Lys Glu Thr Leu Val Glu Pro Gly Ser Phe Ser Gln
785                 790                 795                 800
Gln Asn Gly Asp His Pro Lys Pro Ala Leu Asp Thr Gly Tyr Glu Thr
                805                 810                 815
Glu Gln Asp Thr Ile Thr Ser Lys Val Pro Thr Asp Arg Glu Asp Ser
            820                 825                 830
Gln Arg Ile Asp Glu Leu Ser Ala Arg Asp Lys Pro Phe Asp Val Lys
        835                 840                 845
Cys Glu Leu Lys Phe Ala Asp Ser Asp Ala Asp Gly Asp
        850                 855                 860
```

<210> SEQ ID NO 3
<211> LENGTH: 30
<212> TYPE: DNA
<213> ORGANISM: Artificial
<220> FEATURE:
<223> OTHER INFORMATION: Polynucleotide anti-CD100 VH CDR1

<400> SEQUENCE: 3
ggctacagct tcagcgacta ctacatgcac                               30

<210> SEQ ID NO 4
<211> LENGTH: 51
<212> TYPE: DNA
<213> ORGANISM: Artificial
<220> FEATURE:
<223> OTHER INFORMATION: Polynucleotide anti-CD100 VH CDR2

<400> SEQUENCE: 4
cagattaatc ctaccactgg cggcgctagc tacaaccaga agttcaaggg c        51

<210> SEQ ID NO 5
<211> LENGTH: 27
<212> TYPE: DNA
<213> ORGANISM: Artificial
<220> FEATURE:
<223> OTHER INFORMATION: Polynucleotide anti-CD100 VH CDR3

<400> SEQUENCE: 5
tattactacg gcagacactt cgatgtc                                  27

<210> SEQ ID NO 6
<211> LENGTH: 10
<212> TYPE: PRT
<213> ORGANISM: Artificial
<220> FEATURE:
<223> OTHER INFORMATION: Polypeptide anti-CD100 VH CDR1

<400> SEQUENCE: 6

Gly Tyr Ser Phe Ser Asp Tyr Tyr Met His
1               5                   10

<210> SEQ ID NO 7
<211> LENGTH: 17
<212> TYPE: PRT
<213> ORGANISM: Artificial
<220> FEATURE:
<223> OTHER INFORMATION: Polypeptide anti-CD100 VH CDR2

<400> SEQUENCE: 7

Gln Ile Asn Pro Thr Thr Gly Gly Ala Ser Tyr Asn Gln Lys Phe Lys
1               5                   10                  15

Gly

<210> SEQ ID NO 8
<211> LENGTH: 9
<212> TYPE: PRT
<213> ORGANISM: Artificial
<220> FEATURE:
<223> OTHER INFORMATION: Polypeptide anti-CD100 VH CDR3

<400> SEQUENCE: 8

Tyr Tyr Tyr Gly Arg His Phe Asp Val
1               5

<210> SEQ ID NO 9
<211> LENGTH: 118
<212> TYPE: PRT
<213> ORGANISM: Artificial
<220> FEATURE:
<223> OTHER INFORMATION: Polypeptide anti-CD100 VH 2503

<400> SEQUENCE: 9

```
Gln Val Gln Leu Val Gln Ser Gly Ala Glu Val Lys Pro Gly Ser
1               5                   10                  15

Ser Val Lys Val Ser Cys Lys Ala Ser Gly Tyr Ser Phe Ser Asp Tyr
                20                  25                  30

Tyr Met His Trp Val Arg Gln Ala Pro Gly Gln Gly Leu Glu Trp Met
            35                  40                  45

Gly Gln Ile Asn Pro Thr Thr Gly Gly Ala Ser Tyr Asn Gln Lys Phe
        50                  55                  60

Lys Gly Lys Ala Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Tyr Gly Arg His Phe Asp Val Trp Gly Gln Gly Thr
            100                 105                 110

Thr Val Thr Val Ser Ser
        115
```

<210> SEQ ID NO 10
<211> LENGTH: 118
<212> TYPE: PRT
<213> ORGANISM: Artificial
<220> FEATURE:
<223> OTHER INFORMATION: Polypeptide anti-CD100 VH 67

<400> SEQUENCE: 10

```
Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Ser Asp Tyr
                20                  25                  30

Tyr Met His Trp Val Lys Gln Ser Pro Glu Asn Ser Leu Glu Trp Ile
            35                  40                  45

Gly Gln Ile Asn Pro Thr Thr Gly Gly Ala Ser Tyr Asn Gln Lys Phe
        50                  55                  60

Lys Gly Lys Ala Thr Leu Thr Val Asp Lys Ser Ser Ser Thr Ala Tyr
65                  70                  75                  80

Met Gln Leu Lys Ser Leu Thr Ser Glu Glu Ser Ala Val Tyr Tyr Cys
                85                  90                  95

Thr Arg Tyr Tyr Tyr Gly Arg His Phe Asp Val Trp Gly Gln Gly Thr
            100                 105                 110

Thr Val Thr Val Ser Ser
        115
```

<210> SEQ ID NO 11
<211> LENGTH: 45
<212> TYPE: DNA
<213> ORGANISM: Artificial
<220> FEATURE:
<223> OTHER INFORMATION: Polynucleotide anti-CD100 VL CDR1

<400> SEQUENCE: 11
aaggccagcc aaagcgtgga ttatgatggc gatagctata tgaac          45

```
<210> SEQ ID NO 12
<211> LENGTH: 21
<212> TYPE: DNA
<213> ORGANISM: Artificial
<220> FEATURE:
<223> OTHER INFORMATION: Polynucleotide anti-CD100 VL CDR2

<400> SEQUENCE: 12
gctgcatcca atctggaaag c                                           21

<210> SEQ ID NO 13
<211> LENGTH: 27
<212> TYPE: DNA
<213> ORGANISM: Artificial
<220> FEATURE:
<223> OTHER INFORMATION: Polynucleotide anti-CD100 VL CDR3

<400> SEQUENCE: 13
cagcaaagca atgaggatcc ctacacc                                     27

<210> SEQ ID NO 14
<211> LENGTH: 15
<212> TYPE: PRT
<213> ORGANISM: Artificial
<220> FEATURE:
<223> OTHER INFORMATION: Polypeptide anti-CD100 VL CDR1

<400> SEQUENCE: 14

Lys Ala Ser Gln Ser Val Asp Tyr Asp Gly Asp Ser Tyr Met Asn
1               5                   10                  15

<210> SEQ ID NO 15
<211> LENGTH: 7
<212> TYPE: PRT
<213> ORGANISM: Artificial
<220> FEATURE:
<223> OTHER INFORMATION: Polypeptide anti-CD100 VL CDR2

<400> SEQUENCE: 15

Ala Ala Ser Asn Leu Glu Ser
1               5

<210> SEQ ID NO 16
<211> LENGTH: 9
<212> TYPE: PRT
<213> ORGANISM: Artificial
<220> FEATURE:
<223> OTHER INFORMATION: Polypeptide anti-CD100 VL CDR3

<400> SEQUENCE: 16

Gln Gln Ser Asn Glu Asp Pro Tyr Thr
1               5

<210> SEQ ID NO 17
<211> LENGTH: 111
<212> TYPE: PRT
<213> ORGANISM: Artificial
<220> FEATURE:
<223> OTHER INFORMATION: Polypeptide anti-CD100 VL 2503

<400> SEQUENCE: 17

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Asp
            20                  25                  30
```

Gly Asp Ser Tyr Met Asn Trp Tyr Gln Gln Lys Pro Gly Gln Pro Pro
            35                  40                  45

Lys Leu Leu Ile Tyr Ala Ala Ser Asn Leu Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ser Asn
                 85                  90                  95

Glu Asp Pro Tyr Thr Phe Gly Gln Gly Thr Lys Leu Glu Ile Lys
            100                 105                 110

<210> SEQ ID NO 18
<211> LENGTH: 111
<212> TYPE: PRT
<213> ORGANISM: Artificial
<220> FEATURE:
<223> OTHER INFORMATION: Polypeptide anti-CD100 VL 67

<400> SEQUENCE: 18

Asp Ile Val Met Thr Gln Ser Pro Ala Ser Leu Ala Val Ser Leu Gly
 1               5                  10                  15

Gln Arg Ala Thr Ile Ser Cys Lys Ala Ser Gln Ser Val Asp Tyr Asp
             20                  25                  30

Gly Asp Ser Tyr Met Asn Trp Tyr Gln Gln Lys Pro Gly Gln Pro Pro
            35                  40                  45

Lys Leu Leu Ile Tyr Ala Ala Ser Asn Leu Glu Ser Gly Ile Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln Gln Ser Asn
                 85                  90                  95

Glu Asp Pro Tyr Thr Phe Gly Gly Gly Thr Lys Leu Glu Ile Lys
            100                 105                 110

<210> SEQ ID NO 19
<211> LENGTH: 354
<212> TYPE: DNA
<213> ORGANISM: Artificial
<220> FEATURE:
<223> OTHER INFORMATION: Polynucleotide anti-CD100 VH 2503

<400> SEQUENCE: 19
caggtgcagc tggtgcagag cggcgctgag gtgaagaagc ctggcagcag cgtgaaggtc     60
tcctgcaagg ctagcggcta cagcttcagc gactactaca tgcactgggt gagacaggcc    120
cctggccaag gcctggagtg gatgggccag attaatccta ccactggcgg cgctagctac    180
aaccagaagt tcaagggcaa ggccaccatt accgtggaca aaagcaccag cacagcctac    240
atggagctga gcagcctgag aagcgaggac accgccgtgt attactgtgc cagatattac    300
tacggcagac acttcgatgt ctggggccaa ggcaccacgg tcaccgtctc ttca          354

<210> SEQ ID NO 20
<211> LENGTH: 354
<212> TYPE: DNA
<213> ORGANISM: Artificial
<220> FEATURE:
<223> OTHER INFORMATION: Polynucleotide anti-CD100 VH 67

<400> SEQUENCE: 20
caggtccagc tgcagcagtc tggacctgag ctggtgaagc ctggggcttc agtgaagata     60

```
tcctgcaagg cttctggtta ctcattcagt gactactaca tgcactgggt gaagcaaagt      120
cctgaaaata gtcttgagtg gattggacag attaatccta ccactggggg tgctagctac      180
aaccagaagt tcaagggcaa ggccacatta actgtagata atcctccag cacagcctac       240 atgcagctca agagcctgac atctgaagag tctgcagtct attactgtac aagatattac      300
tacggtagac acttcgatgt ctggggccaa gggaccacgg tcaccgtttc ctca            354
```

<210> SEQ ID NO 21
<211> LENGTH: 333
<212> TYPE: DNA
<213> ORGANISM: Artificial
<220> FEATURE:
<223> OTHER INFORMATION: Polynucleotide anti-CD100 VL 2503

<400> SEQUENCE: 21

```
gacatcgtga tgacccagag cccagacagc ctggctgtga gcctgggcga gagggccacc      60
atcaactgca aggccagcca aagcgtggat tatgatggcg atagctatat gaactggtac      120
cagcagaaac caggccagcc tcctaagctg ctgatttacg ctgcatccaa tctggaaagc      180
ggcgtgcctg acagattcag cggcagcggc agcggcacag atttcactct gaccatcagc      240
agcctgcagg ctgaagatgt ggcagtgtat tactgtcagc aaagcaatga ggatccctac      300
accttcggcc aagggaccaa gctcgagatc aaa                                   333
```

<210> SEQ ID NO 22
<211> LENGTH: 333
<212> TYPE: DNA
<213> ORGANISM: Artificial
<220> FEATURE:
<223> OTHER INFORMATION: Polynucleotide anti-CD100 VL 67

<400> SEQUENCE: 22

```
gacattgtga tgacccagtc tccagcttct ttggctgtgt ctctagggca gagggccacc      60
atctcctgca aggccagcca agtgttgat tatgatggtg atagttatat gaactggtac       120
caacagaaac caggacagcc acccaaactc ctcatctatg ctgcatccaa tctagaatct      180
gggatcccag ccaggtttag tggcagtggg tctgggacag acttcaccct caacatccat      240
cctgtggagg aggaggatgc tgcaacctat tactgtcagc aaagtaatga ggatccgtac      300
acgttcggag gggggaccaa gctcgagatc aaa                                   333
```

<210> SEQ ID NO 23
<211> LENGTH: 2586
<212> TYPE: DNA
<213> ORGANISM: Homo sapiens

<400> SEQUENCE: 23

```
atgaggatgt gcacccccat taggggggctg ctcatggccc ttgcagtgat gtttgggaca     60
gcgatggcat ttgcacccat accccggatc acctgggagc acagagaggt gcacctggtg      120
cagtttcatg agccagacat ctacaactac tcagccttgc tgctgagcga ggacaaggac      180
accttgtaca taggtgcccg ggaggcggtc ttcgctgtga acgcactcaa catctccgag      240
aagcagcatg aggtgtattg gaaggtctca aagacaaaa aagcaaaatg tgcagaaaag      300
gggaaatcaa aacagacaga gtgcctcaac tacatccggg tgctgcagcc actcagcgcc      360
acttcccttt acgtgtgtgg gaccaacgca ttccagccgg cctgtgacca cctgaactta      420
acatccttta gtttctgggg aaaaatgaa gatggcaaag gaagatgtcc ctttgaccca      480
```

|  |  |
|---|---|
| gcacacagct acacatccgt catggttgat ggagaacttt attcgggac gtcgtataat | 540 |
| tttttgggaa gtgaacccat catctcccga aattcttccc acagtcctct gaggacagaa | 600 |
| tatgcaatcc cttggctgaa cgagcctagt ttcgtgtttg ctgacgtgat ccgaaaaagc | 660 |
| ccagacagcc ccgacggcga ggatgacagg gtctacttct tcttcacgga ggtgtctgtg | 720 |
| gagtatgagt ttgtgttcag ggtgctgatc ccacggatag caagagtgtg caaggggac | 780 |
| cagggcggcc tgaggaccttt gcagaagaaa tggacctcct tcctgaaagc ccgactcatc | 840 |
| tgctcccggc cagacagcgg cttggtcttc aatgtgctgc gggatgtctt cgtgctcagg | 900 |
| tccccgggcc tgaaggtgcc tgtgttctat gcactcttca ccccacagct gaacaacgtg | 960 |
| gggctgtcgg cagtgtgcgc ctacaacctg tccacagccg aggaggtctt ctcccacggg | 1020 |
| aagtacatgc agagccaccac agtggagcag tcccacacca gtgggtgcg ctataatggc | 1080 |
| ccggtaccca agccgcggcc tggagcgtgc atcgacagcg aggcacgggc cgccaactac | 1140 |
| accagctcct tgaatttgcc agacaagacg ctgcagttcg ttaaagacca ccctttgatg | 1200 |
| gatgactcgg taaccccaat agacaacagg cccaggttaa tcaagaaaga tgtgaactac | 1260 |
| acccagatcg tggtggaccg gacccaggcc ctggatggga ctgtctatga tgtcatgttt | 1320 |
| gtcagcacag accggggagc tctgcacaaa gccatcagcc tcgagcacgc tgttcacatc | 1380 |
| atcgaggaga cccagctctt ccaggacttt gagccagtcc agaccctgct gctgtcttca | 1440 |
| aagaagggca acaggtttgt ctatgctggc tctaactcgg gcgtggtcca ggccccgctg | 1500 |
| gccttctgtg ggaagcacgg cacctgcgag gactgtgtgc tggcgcggga ccctactgc | 1560 |
| gcctggagcc cgcccacagc gacctgcgtg gctctgcacc agaccgagag ccccagcagg | 1620 |
| ggtttgattc aggagatgag cggcgatgct tctgtgtgcc cggataaaag taaggaagt | 1680 |
| taccggcagc attttttcaa gcacggtggc acagcggaac tgaaatgctc ccaaaaatcc | 1740 |
| aacctggccc gggtcttttg gaagttccag aatggcgtgt tgaaggccga gagccccaag | 1800 |
| tacggtctta tgggcagaaa aaacttgctc atcttcaact tgtcagaagg agacagtggg | 1860 |
| gtgtaccagt gcctgtcaga ggagagggtt aagaacaaaa cggtcttcca agtggtcgcc | 1920 |
| aagcacgtcc tggaagtgaa ggtggttcca agcccgtag tggcccccac cttgtcagtt | 1980 |
| gttcagacag aaggtagtag gattgccacc aaagtgttgg tggcatccac ccaagggtct | 2040 |
| tctcccccaa ccccagccgt gcaggccacc tcctccgggg ccatcaccct tcctcccaag | 2100 |
| cctgcgccca ccggcacatc ctgcgaacca agatcgtca tcaacacggt ccccagctc | 2160 |
| cactcggaga aaaccatgta tcttaagtcc agcgacaacc gcctcctcat gtccctcttc | 2220 |
| ctcttcttct tgttctctt cctctgcctc ttttcctaca actgctataa gggatacctg | 2280 |
| cccagacagt gcttgaaatt ccgctcggcc ctactaattg ggaagaagaa gcccaagtca | 2340 |
| gatttctgtg accgtgagca gagcctgaag gagacgttag tagagccagg gagcttctcc | 2400 |
| cagcagaatg gggagcaccc caagccagcc ctggacaccg gctatgagac cgagcaagac | 2460 |
| accatcacca gcaaagtccc cacgataggg aggactcac agaggatcga cgacctttct | 2520 |
| gccagggaca agcccttga cgtcaagtgt gagctgaagt tcgctgactc agacgcagat | 2580 |
| ggagac | 2586 |

<210> SEQ ID NO 24
<211> LENGTH: 13
<212> TYPE: PRT
<213> ORGANISM: Artificial
<220> FEATURE:
<223> OTHER INFORMATION: Peptide epitope of proteolipid protein -continued

```
        PLP(139-151)

<400> SEQUENCE: 24

His Ser Leu Gly Lys Trp Leu Gly His Pro Asp Lys Phe
1               5                   10

<210> SEQ ID NO 25
<211> LENGTH: 118
<212> TYPE: PRT
<213> ORGANISM: Artificial
<220> FEATURE:
<223> OTHER INFORMATION: Polypeptide anti-CD100 VH 76

<400> SEQUENCE: 25

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Arg Tyr
            20                  25                  30

Trp Met His Trp Val Lys Gln Arg Pro Gly Gln Gly Leu Glu Trp Ile
        35                  40                  45

Gly Tyr Ile Asn Pro Ser Thr Gly Tyr Ser Asp Tyr Asn Gln Lys Phe
    50                  55                  60

Lys Asp Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Pro Tyr Gly Trp Thr Met Asp Ser Trp Gly Gln Gly Thr
            100                 105                 110

Leu Val Thr Val Ser Ser
        115

<210> SEQ ID NO 26
<211> LENGTH: 10
<212> TYPE: PRT
<213> ORGANISM: Artificial
<220> FEATURE:
<223> OTHER INFORMATION: Polypeptide anti-CD100 VH 76 CDR1

<400> SEQUENCE: 26

Gly Tyr Thr Phe Thr Arg Tyr Trp Met His
1               5                   10

<210> SEQ ID NO 27
<211> LENGTH: 17
<212> TYPE: PRT
<213> ORGANISM: Artificial
<220> FEATURE:
<223> OTHER INFORMATION: Polypeptide anti-CD100 VH 76 CDR2

<400> SEQUENCE: 27

Tyr Ile Asn Pro Ser Thr Gly Tyr Ser Asp Tyr Asn Gln Lys Phe Lys
1               5                   10                  15

Asp

<210> SEQ ID NO 28
<211> LENGTH: 9
<212> TYPE: PRT
<213> ORGANISM: Artificial
<220> FEATURE:
<223> OTHER INFORMATION: Polypeptide anti-CD100 VH 76 CDR3

<400> SEQUENCE: 28
```

```
Asp Pro Tyr Gly Trp Thr Met Asp Ser
1               5
```

<210> SEQ ID NO 29
<211> LENGTH: 107
<212> TYPE: PRT
<213> ORGANISM: Artificial
<220> FEATURE:
<223> OTHER INFORMATION: Polypeptide anti-CD100 VL 76

<400> SEQUENCE: 29

```
Asp Ile Gln Met Thr Gln Ser Pro Ser Ser Leu Ser Ala Ser Leu Gly
1               5                   10                  15

Asp Thr Ile Thr Ile Thr Cys His Ala Ser Gln Asn Ile Asn Val Trp
            20                  25                  30

Leu Ser Trp Tyr Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Tyr
                85                  90                  95

Thr Phe Gly Gly Gly Thr Lys Leu Glu Ile Lys
            100                 105
```

<210> SEQ ID NO 30
<211> LENGTH: 11
<212> TYPE: PRT
<213> ORGANISM: Artificial
<220> FEATURE:
<223> OTHER INFORMATION: Polypeptide anti-CD100 VL 76 CDR1

<400> SEQUENCE: 30

```
His Ala Ser Gln Asn Ile Asn Val Trp Leu Ser
1               5                   10
```

<210> SEQ ID NO 31
<211> LENGTH: 7
<212> TYPE: PRT
<213> ORGANISM: Artificial
<220> FEATURE:
<223> OTHER INFORMATION: Polypeptide anti-CD100 VL 76 CDR2

<400> SEQUENCE: 31

```
Lys Ala Ser Asn Leu His Thr
1               5
```

<210> SEQ ID NO 32
<211> LENGTH: 9
<212> TYPE: PRT
<213> ORGANISM: Artificial
<220> FEATURE:
<223> OTHER INFORMATION: Polypeptide anti-CD100 VL 76 CDR3

<400> SEQUENCE: 32

```
Gln Gln Gly Gln Ser Tyr Pro Tyr Thr
1               5
```

<210> SEQ ID NO 33
<211> LENGTH: 354
<212> TYPE: DNA
<213> ORGANISM: Artificial
<220> FEATURE:

<223> OTHER INFORMATION: Polynucleotide anti-CD100 VH 76

<400> SEQUENCE: 33

```
caggtccagc tgcagcagtc tggggctgaa ctggcaaaac ctggggcctc agtgaagatg      60
tcctgcaagg cttctggcta cacctttact aggtactgga tgcactgggt aaaacagagg     120
cctggacagg gtctggaatg gattggatac attaatccta gcactggtta ttctgattac     180
aatcagaagt tcaaggacaa ggccacattg actgcagaca atcctccag cacagcctac      240
atgcaactga gcagcctgac atctgaggac tctgcagtct attactgtgc aagagacccc     300
tacggctgga ctatggactc ctggggccaa gggactctgg tcaccgtctc ctca            354
```

<210> SEQ ID NO 34
<211> LENGTH: 30
<212> TYPE: DNA
<213> ORGANISM: Artificial
<220> FEATURE:
<223> OTHER INFORMATION: Polynucleotide anti-CD100 VH 76 CDR1

<400> SEQUENCE: 34

```
ggctacacct ttactaggta ctggatgcac                                       30
```

<210> SEQ ID NO 35
<211> LENGTH: 51
<212> TYPE: DNA
<213> ORGANISM: Artificial
<220> FEATURE:
<223> OTHER INFORMATION: Polynucleotide anti-CD100 VH 76 CDR2

<400> SEQUENCE: 35

```
tacattaatc ctagcactgg ttattctgat acaatcaga agttcaagga c                51
```

<210> SEQ ID NO 36
<211> LENGTH: 27
<212> TYPE: DNA
<213> ORGANISM: Artificial
<220> FEATURE:
<223> OTHER INFORMATION: Polynucleotide anti-CD100 VH 76 CDR3

<400> SEQUENCE: 36

```
gacccctacg gctggactat ggactcc                                          27
```

<210> SEQ ID NO 37
<211> LENGTH: 321
<212> TYPE: DNA
<213> ORGANISM: Artificial
<220> FEATURE:
<223> OTHER INFORMATION: Polynucleotide anti-CD100 VL 76

<400> SEQUENCE: 37

```
gacatccaga tgacccagtc tccatccagt ctgtctgcat cccttggaga cacaattacc      60
atcacttgcc atgccagtca gaacattaat gtttggttaa ctggtacca gcagaaacca     120
ggaaatattc ctaaactatt gatctataag gcttccaact gcacacagg cgtcccatca      180
aggtttagtg gcagtggatc tggaacaggt ttcacattaa ccatcagcag cctgcagcct     240
gaagacattg ccacttacta ctgtcaacag ggtcaaagtt atccgtacac gttcggaggg     300
gggaccaagc tcgagatcaa a                                                321
```

<210> SEQ ID NO 38
<211> LENGTH: 33
<212> TYPE: DNA
<213> ORGANISM: Artificial

```
<220> FEATURE:
<223> OTHER INFORMATION: Polynucleotide anti-CD100 VL 76 CDR1

<400> SEQUENCE: 38
catgccagtc agaacattaa tgtttggtta agc                                    33

<210> SEQ ID NO 39
<211> LENGTH: 21
<212> TYPE: DNA
<213> ORGANISM: Artificial
<220> FEATURE:
<223> OTHER INFORMATION: Polynucleotide anti-CD100 VL 76 CDR2

<400> SEQUENCE: 39
aaggcttcca acttgcacac a                                                 21

<210> SEQ ID NO 40
<211> LENGTH: 27
<212> TYPE: DNA
<213> ORGANISM: Artificial
<220> FEATURE:
<223> OTHER INFORMATION: Polynucleotide anti-CD100 VL 76 CDR3

<400> SEQUENCE: 40
caacagggtc aaagttatcc gtacacg                                           27

<210> SEQ ID NO 41
<211> LENGTH: 51
<212> TYPE: DNA
<213> ORGANISM: Artificial
<220> FEATURE:
<223> OTHER INFORMATION: Epitope 1

<400> SEQUENCE: 41
ctgaaggtgc ctgtgttcta tgcactcttc accccacagc tgaacaacgt g                51

<210> SEQ ID NO 42
<211> LENGTH: 17
<212> TYPE: PRT
<213> ORGANISM: Artificial
<220> FEATURE:
<223> OTHER INFORMATION: Epitope 1

<400> SEQUENCE: 42

Leu Lys Val Pro Val Phe Tyr Ala Leu Phe Thr Pro Gln Leu Asn Asn
1               5                   10                  15
Val

<210> SEQ ID NO 43
<211> LENGTH: 45
<212> TYPE: DNA
<213> ORGANISM: Artificial
<220> FEATURE:
<223> OTHER INFORMATION: Epitope 2

<400> SEQUENCE: 43
aaatggacct ccttcctgaa agcccgactc atctgctccc ggcca                       45

<210> SEQ ID NO 44
<211> LENGTH: 15
<212> TYPE: PRT
<213> ORGANISM: Artificial
<220> FEATURE:
<223> OTHER INFORMATION: Epitope 2

<400> SEQUENCE: 44
```

```
<210> SEQ ID NO 45
<211> LENGTH: 42
<212> TYPE: DNA
<213> ORGANISM: Artificial
<220> FEATURE:
<223> OTHER INFORMATION: Epitope 3

<400> SEQUENCE: 45
gagtttgtgt tcagggtgct gatcccacgg atagcaagag tg            42

<210> SEQ ID NO 46
<211> LENGTH: 14
<212> TYPE: PRT
<213> ORGANISM: Artificial
<220> FEATURE:
<223> OTHER INFORMATION: Epitope 3

<400> SEQUENCE: 46

Glu Phe Val Phe Arg Val Leu Ile Pro Arg Ile Ala Arg Val
1               5                   10

<210> SEQ ID NO 47
<211> LENGTH: 113
<212> TYPE: PRT
<213> ORGANISM: Artificial sequence
<220> FEATURE:
<223> OTHER INFORMATION: 2282 VL domain

<400> SEQUENCE: 47

Asp Ile Val Met Thr Gln Ser Pro Leu Ser Leu Pro Val Ser Pro Gly
1               5                   10                  15

Glu Pro Ala Thr Ile Asn Cys Lys Ser Ser Gln Ser Leu Phe Asn Ser
                20                  25                  30

Gly Asn Gln Lys Asn Tyr Leu Ala Trp Tyr Leu Gln Lys Pro Gly Gln
            35                  40                  45

Pro Pro Lys Leu Leu Ile Tyr Gly Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp His Thr Tyr Pro Tyr Thr Phe Gly Gln Gly Thr Lys Leu Glu Ile
                100                 105                 110

Lys

<210> SEQ ID NO 48
<211> LENGTH: 122
<212> TYPE: PRT
<213> ORGANISM: Artificial sequence
<220> FEATURE:
<223> OTHER INFORMATION: 2282 VH domain

<400> SEQUENCE: 48

Gln Val Gln Leu Val Gln Ser Gly Ala Glu Val Lys Lys Pro Gly Ser
1               5                   10                  15

Ser Val Lys Val Ser Cys Thr Ala Ser Gly Tyr Thr Phe Thr Asp Tyr
                20                  25                  30

Tyr Met Asp Trp Val Arg Gln Ala Pro Gly Gln Gly Leu Glu Trp Met
```

Lys Trp Thr Ser Phe Leu Lys Ala Arg Leu Ile Ala Ser Arg Pro
1               5                   10                  15

```
                35                    40                    45
Gly Arg Val Asn Pro Tyr His Gly Tyr Ala Thr Tyr Asn Gln Lys Phe
            50                    55                    60

Lys Gly Arg Val Thr Ile Thr Ala Asp Lys Ser Thr Ser Thr Ala Tyr
 65                    70                    75                    80

Met Glu Leu Ser Ser Leu Arg Ser Glu Asp Thr Ala Val Tyr Tyr Cys
                85                    90                    95

Ala Arg Glu Glu Asn Ser Tyr Asp Gly Tyr Tyr Gly Met Asp Tyr Trp
            100                   105                   110

Gly Gln Gly Thr Leu Val Thr Val Ser Ser
            115                   120
```

USE OF SEMAPHORIN-4D BINDING MOLECULES FOR TREATMENT OF ATHEROSCLEROSIS

CROSS-REFERENCE TO RELATED APPLICATIONS

This U.S. non-provisional patent application claims the benefit of U.S. Provisional Patent Application No. 61/889,421, filed Oct. 10, 2013, which is incorporated herein by reference in its entirety.

REFERENCE TO SEQUENCE LISTING SUBMITTED ELECTRONICALLY

The content of the electronically submitted sequence listing in ASCII text file (Name: "Sequence_Listing_58008_136614.txt"; Size: 36,964 bytes; and Date of Creation: Oct. 9, 2014) filed with the application is incorporated herein by reference in its entirety.

BACKGROUND OF THE INVENTION

Semaphorin 4D (SEMA4D), also known as CD100, is a transmembrane protein (e.g., SEQ ID NO: 1 (human); SEQ ID NO: 2 (murine)) that belongs to the class IV semaphorin gene family. SEMA4D is expressed on the cell surface as a homodimer, but upon cell activation SEMA4D can be released from the cell surface via proteolytic cleavage to generate sSEMA4D, a soluble form of the protein, which is also biologically active. See Suzuki et al., *Nature Rev. Immunol.* 3:159-167 (2003); Kikutani et al., *Nature Immunol.* 9:17-23 (2008).

SEMA4D is expressed at high levels in lymphoid organs, including the spleen, thymus, and lymph nodes, and in non-lymphoid organs, such as the brain, heart, and kidney. In lymphoid organs, SEMA4D is abundantly expressed on resting T cells but only weakly expressed on resting B cells and antigen-presenting cells (APCs), such as dendritic cells (DCs). Its expression, however, is upregulated in these cells following activation by various immunological stimuli. The release of soluble SEMA4D from immune cells is also increased by cell activation.

Atherosclerosis has been recognized as an inflammatory disease in which the immune cells play crucial roles during disease progression (Hansson G K et al., *Nat Rev Immunol* 6: 508-519, 2006). Macrophages express CD40 molecules and T cells have CD40 ligand (CD40L or CD154) on their cell surfaces (Mach F et al., *Circulation* 96: 396-399, 1997; and Mach F et al., *Proc Natl Acad Sci USA* 94: 1931-36, 1997). CD40 ligation with CD40L on intraplaque immune cells induces the secretion of proteases and pro-inflammatory mediators, which expands inflammatory activation (Mach F et al., *Circulation* 96: 396-399, 1997). Blockade of CD40 ligation or a CD40L gene knockout can retard atherosclerotic plaque development in atherosclerosis-prone mice (Mach F et al., *Nature* 394: 200-203, 1998; and Lutgens E et al., *Nat Med* 11: 1313-1316, 1999). CD40 ligation on immune cells with stimulating anti-CD40 antibodies has been reported to induce the expression of Sema4D (CD100) (Kumanogoh A et al., *Immunity* 13: 621-31, 2000).

SEMA4D has been implicated in various processes such as enhancing the immune response, angiogenesis, epithelial morphogenesis and bone remodeling (Kruger R P et al., *Nat Rev Mol Cell Biol* 6: 789-800, 2005; Pasterkamp R. J., *Nat Rev Neurosci* 13:605-618, 2012; and Kang S et al., *Seminars in Cell & Dev Biol* 24:163-171, 2013). Lymphocytes, macrophages, endothelial cells and platelets in atherosclerotic plaques express plexin-B1 on their membrane surface, a high affinity receptor for Sema4D (Basile J R et al., *Moll Cell Biol* 25: 6889-6898, 2005; Delaire S et al., *J Immunol* 166: 4348-4354, 2001; and Chabbert-de Ponnat I et al., *Int Immunol* 17: 439-447, 2005). Sema4D expressed by T cells or released from the T cell membrane can, therefore, have certain effects on cells located in atherosclerotic plaques (Basile J R et al., *Mol. Cell Biol* 25: 6889-6898, 2005; Delaire S et al., *J Immunol* 166: 4348-4354, 2001; and Chabbert-de Ponnat I et al., *Int Immunol* 17: 439-447, 2005). Previous studies revealed pro-angiogenic activity of Sema4D on endothelial cells in vitro and in vivo (Conrotto P et al., *Blood* 105: 4321-4329, 2005; and Basil J R et al., *Cancer Res* 64: 5212-5224, 2004.). Moreover, high level of expression of Sema4D was observed in several squamous cell carcinomas suggesting a critical role of Sema4D in tumor-induced angiogenesis in vivo (Basile J R et al., *Proc Natl Acad Sci USA* 103: 9017-9022, 2006.). Thus, Sema4D can affect plaque growth by, e.g., promoting the neovascularization process occurring in atheroma. In fact, one study revealed that deleting the Sema4D gene in atherosclerosis-prone ApoE deficient (ApoE−/−) mice delayed the growth of atherosclerotic plaques and neovascularization in the plaque area, suggesting that blocking the Sema4D signal during the progression phase of atherosclerosis can prevent the plaque growth and neovascularization (Yukawa K et al., *Int. J Mol. Med.* 26: 39-44, 2010).

BRIEF SUMMARY OF THE INVENTION

Methods for using semaphorin 4D binding molecules for treatment of atherosclerosis are disclosed herein. According to aspects of the invention illustrated herein, there is provided a method for reducing, inhibiting, suppressing and/or delaying atherosclerotic plaque formation in a subject having atherosclerosis including administering to the subject an effective amount of an isolated binding molecule which specifically binds to and blocks the activity of semaphorin 4D (SEMA4D). In certain embodiments, methods for inhibiting, suppressing, reducing or delaying growth of atherosclerotic plaques in a subject having atherosclerosis, comprising administering to the subject an effective amount of an isolated binding molecule which specifically binds to Semaphorin-4D (SEMA4D) are provided. In certain embodiments, the binding molecule inhibits SEMA4D interaction with its receptor. In certain embodiments, the receptor is Plexin-B1 or Plexin-B2. In certain embodiments, the binding molecule inhibits SEMA4D-mediated Plexin-B1 signal transduction. In certain embodiments of any of the aforementioned methods, the subject has cardiovascular disease. In certain embodiments, the cardiovascular disease is selected from the group consisting of coronary heart disease (also ischemic heart disease or coronary artery disease), cardiomyopathy, hypertensive heart disease, heart failure, cor pulmonale, cardiac dysrhythmias, inflammatory heart disease endocarditis, inflammatory cardiomegaly, myocarditis, valvular heart disease, cerebrovascular disease, peripheral arterial disease, congenital heart disease, rheumatic heart disease, and a combination thereof. In certain embodiments of any of the aforementioned methods, the isolated binding molecule specifically binds to the same SEMA4D epitope as a reference monoclonal antibody VX15/2503 or 67. In certain embodiments of any of the aforementioned methods, the isolated binding molecule competitively inhibits a reference monoclonal antibody VX15/2503 or 67 from specifically binding to SEMA4D. In certain embodiments of any of the aforementioned methods, the isolated binding molecule comprises an antibody or antigen-binding fragment thereof. In certain embodiments of any of the aforementioned methods, the antibody or antigen-binding fragment thereof comprises a variable heavy chain (VH) comprising VHCDRs 1-3 comprising SEQ ID NOs 6, 7, and 8, respectively, and a variable light chain (VL) comprising VLCDRs 1-3 comprising SEQ ID NOs 14, 15, and 16, respectively. In certain embodiments of any of the aforementioned methods, the VH and VL comprise, respectively, SEQ ID NO: 9 and SEQ ID NO: 17 or SEQ ID NO: 10 and SEQ ID NO: 18. In certain embodiments of any of the aforementioned methods, the method further includes inhibiting, delaying, reducing or delaying neovascularization around the atherosclerotic plaques.

Methods for inhibiting, delaying, reducing or delaying neovascularization in a subject having atherosclerosis, comprising administering to the subject an effective amount of an isolated binding molecule which specifically binds to Semaphorin-4D (SEMA4D) are also provided. In certain embodiments, the binding molecule inhibits SEMA4D interaction with its receptor. In certain embodiments, the receptor is Plexin-B1. In certain embodiments, the binding molecule inhibits SEMA4D-mediated Plexin-B1 signal transduction. In certain embodiments of any of the aforementioned methods, the subject has cardiovascular disease. In certain embodiments, the cardiovascular disease is selected from the group consisting of coronary heart disease (also ischemic heart disease or coronary artery disease), cardiomyopathy, hypertensive heart disease, heart failure, cor pulmonale, cardiac dysrhythmias, inflammatory heart disease endocarditis, inflammatory cardiomegaly, myocarditis, valvular heart disease, cerebrovascular disease, peripheral arterial disease, congenital heart disease, rheumatic heart disease, and a combination thereof. In certain embodiments of any of the aforementioned methods, the isolated binding molecule specifically binds to the same SEMA4D epitope as a reference monoclonal antibody VX15/2503 or 67. In certain embodiments of any of the aforementioned methods, the isolated binding molecule competitively inhibits a reference monoclonal antibody VX15/2503 or 67 from specifically binding to SEMA4D. In certain embodiments of any of the aforementioned methods, the isolated binding molecule comprises an antibody or antigen-binding fragment thereof. In certain embodiments of any of the aforementioned methods, the antibody or antigen-binding fragment thereof comprises a variable heavy chain (VH) comprising VHCDRs 1-3 comprising SEQ ID NOs 6, 7, and 8, respectively, and a variable light chain (VL) comprising VLCDRs 1-3 comprising SEQ ID NOs 14, 15, and 16, respectively. In certain embodiments of any of the aforementioned methods, the VH and VL comprise, respectively, SEQ ID NO: 9 and SEQ ID NO: 17 or SEQ ID NO: 10 and SEQ ID NO: 18.

Methods for treating a subject having atherosclerosis, comprising: administering to a subject determined to have atherosclerotic plaques an effective amount of an isolated binding molecule which specifically binds to Semaphorin-4D (SEMA4D), thereby inhibiting, delaying, reducing or delaying growth of atherosclerotic plaques are also provided. In certain embodiments, the determination is provided by analysis of an image or a sample from the patient. In certain embodiments of any of the aforementioned methods, the patient is determined to have atherosclerotic plaques and is treated if the number, size, or characteristics of atherosclerotic plaques in the patient is above a predetermined threshold number, size, or character. In certain embodiments of any of the aforementioned methods, the patient is determined to have atherosclerotic plaques and is treated if the number, size, or character of atherosclerotic plaques in the patient is indicative of atherosclerosis when compared to one or more control samples. In certain embodiments of any of the aforementioned methods, the patient is determined to have atherosclerotic plaques and is treated if the level of CRP and/or LDL in the sample are above a pre-determined threshold level, are elevated relative to a control sample, or are otherwise indicative of atherosclerotic plaques. In certain embodiments of any of the aforementioned methods, the patient is determined to have atherosclerotic plaques and is treated if imaging determines that the number, size, or character of atherosclerotic plaques are above a pre-determined threshold level, are elevated relative to a control sample, or are otherwise indicative of atherosclerotic plaques. In certain embodiments of the methods, imaging can comprise coronary angiography, intravascular ultrasound (IVUS), carotid ultrasound, coronary computed tomography (CT), magnetic resonance imaging (MRI), positron emission tomography (PET), optical coherence tomography (OCT), near-infrared spectroscopy (NIRS), and NIR fluorescence. In certain embodiments of any of the aforementioned methods, the patient is determined to have atherosclerotic plaques and is treated if the patient is determined to have one or more vulnerable atherosclerotic plaques. In certain embodiments of any of the aforementioned methods, the isolated binding molecule specifically binds to the same SEMA4D epitope as a reference monoclonal antibody VX15/2503 or 67. In certain embodiments of any of the aforementioned methods, the isolated binding molecule competitively inhibits a reference monoclonal antibody VX15/2503 or 67 from specifically binding to SEMA4D. In certain embodiments of any of the aforementioned methods, the isolated binding molecule comprises an antibody or antigen-binding fragment thereof. In certain embodiments of any of the aforementioned methods, the antibody or antigen-binding fragment thereof comprises a variable heavy chain (VH) comprising VHCDRs 1-3 comprising SEQ ID NOs 6, 7, and 8, respectively, and a variable light chain (VL) comprising VLCDRs 1-3 comprising SEQ ID NOs 14, 15, and 16, respectively. In certain embodiments of any of the aforementioned methods, the VH and VL comprise, respectively, SEQ ID NO: 9 and SEQ ID NO: 17 or SEQ ID NO: 10 and SEQ ID NO: 18.

According to aspects illustrated herein, there is provided a method of reducing neovascularization in a subject having atherosclerosis including administering to the subject an effective amount of an isolated binding molecule which specifically binds to semaphorin 4D (SEMA4D).

BRIEF DESCRIPTION OF THE DRAWINGS/FIGURES

FIG. 1A: Inhibited development of atherosclerotic plaques in anti-Sema4D antibody-treated spontaneously hyperlipidemic (SHL) mice with ApoE-deficiency. FIG. 1A shows a quantitative measurement of the sudanophilic area in lipid deposits of atherosclerotic plaque development in SHL mice treated with anti-SEMA4D antibody or isotype control for 12 weeks starting at 14 weeks of age.

Figure 1B:
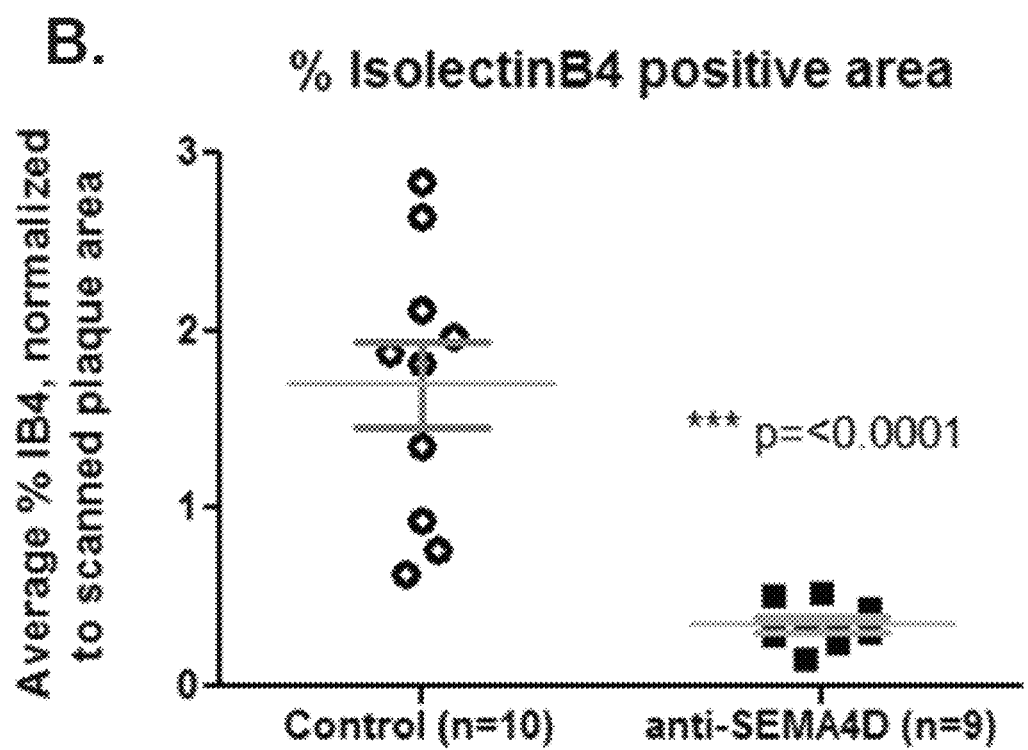
Figure 1C:
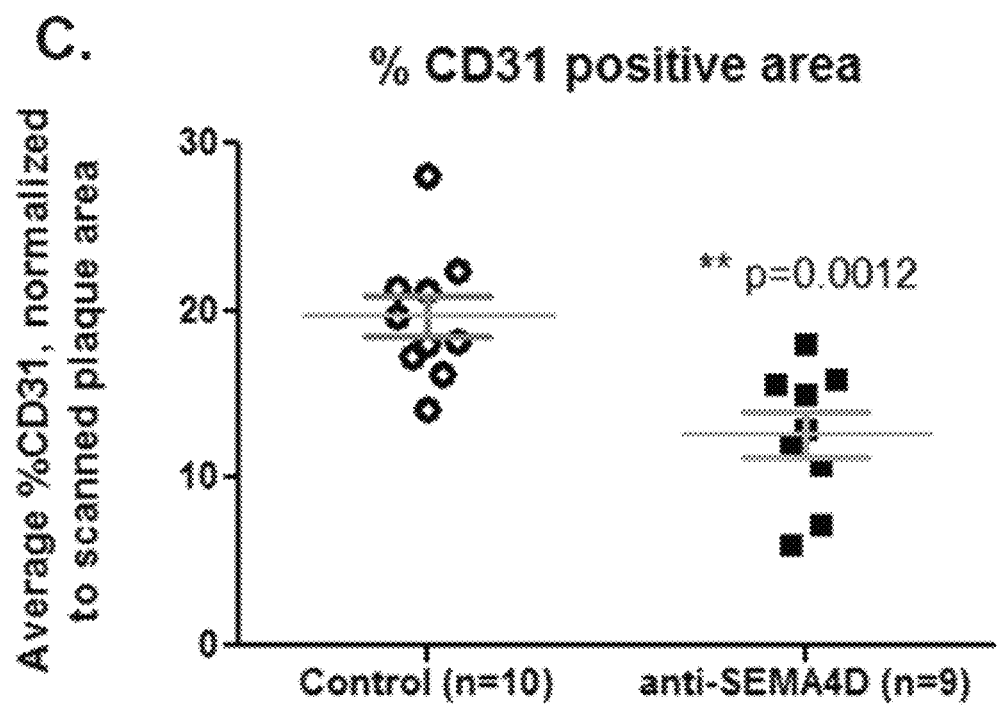

FIGS. 1B and 1C: Reduced neovascularization in plaques of anti-Sema4D antibody-treated SHL mice. FIG. 1B shows neovascularization visualized by a quantitative measurement of isolectin B4 staining of endothelial cells in plaques of anti-Sema4D antibody-treated SHL mice and control antibody-treated SHL mice. FIG. 1C shows endothelial cells in plaques of anti-Sema4D antibody-treated SHL mice and control antibody-treated SHL mice visualized with immunohistochemistry using CD31 antibodies.

DETAILED DESCRIPTION OF THE INVENTION

I. Definitions

It is to be noted that the term "a" or "an" entity refers to one or more of that entity; for example, "an anti-SEMA4D antibody" is understood to represent one or more anti-SEMA4D antibodies. As such, the terms "a" (or "an"), "one or more," and "at least one" can be used interchangeably herein.

As used herein, the term "atherosclerosis" refers to the disorder of the larger arteries that underlies most coronary artery disease, aortic aneurysm, and arterial disease of the lower extremities, and also plays a major role in cerebrovascular disease. Atherosclerosis is a leading cause of death in the United States, both above and below age 65 in both sexes. E. L. Bierman, "Atherosclerosis and Other Forms of Arteriosclerosis," Ch. 208, p. 1 106 in Harrison's Principles of Internal Medicine. 13th edition, eds. K J. Isselbacher, et al. (McGraw-Hill, Inc. NY 1994). Atherosclerosis can affect any artery in the body, including arteries in the heart, brain, arms, legs, pelvis, and kidneys. Atherosclerosis is characterized by infiltration of cholesterol and appearance of foam cells in lesions of the arterial wall. This is followed by a complex sequence of changes involving platelets, macrophages, smooth muscle cells, and growth factors that produces proliferative lesions. These distort the vessels and make them rigid. In individuals with elevated plasma cholesterol levels, there is an increased incidence of atherosclerosis and its complications. W. F. Ganong, Review of Medical Physiology, 17th edition, p. 281 (Appleton & Lange Norwalk, Conn. 1995).

As used herein, the term "neovascularization" or "angiogenesis" refers to the formation of new blood vessels from existing vessels. Neovascularization is present, e.g., in the development of macular degeneration, tumors, cancer, and atherosclerosis.

As used herein, the term "inflammatory disorder" or "inflammatory disease" refers to a disease that is characterized by inflammation and is usually accompanied by redness, swelling, and pain. Inflammation can lead to a host of other diseases, including, but not limited to cardiovascular disease, rheumatoid arthritis, gastroenterological disease, neuroinflammatory diseases (e.g., multiple sclerosis), and even cancer (e.g., gallbladder carcinoma).

As used herein, the term "cardiovascular disease" refers to diseases that involve the heart, the blood vessels (arteries, capillaries, and veins) or both. Examples of cardiovascular diseases include, but are not limited to, coronary heart disease (also ischemic heart disease or coronary artery disease), cardiomyopathy, hypertensive heart disease, heart failure, cor pulmonale, cardiac dysrhythmias, inflammatory heart disease endocarditis, inflammatory cardiomegaly, myocarditis, valvular heart disease, cerebrovascular disease, peripheral arterial disease, congenital heart disease, and rheumatic heart disease.

The term "therapeutically effective amount" refers to an amount of an antibody, polypeptide, polynucleotide, small organic molecule, or other drug effective to "treat" a disease or disorder in a subject or mammal. In the case of a atherosclerosis, the therapeutically effective amount of the drug can delay the formation of atherosclerotic plaques; reduce, retard or stop an increase in new atherosclerotic plaque formation; reduce, suppress, or stop inflammation; inhibit, e.g., suppress, retard, prevent, stop, or reverse neovascularization in, or in the vicinity of atherosclerotic plaques; change in the morphology or function of atherosclerotic plaques; or relieve, to some extent, one or more of the symptoms associated with atherosclerosis; reduce morbidity and mortality; improve quality of life; or any combination of such effects.

Terms such as "treating" or "treatment" or "to treat" or "alleviating" or "to alleviate" refer to both 1) therapeutic measures that cure, slow down, lessen symptoms of, reverse, and/or halt progression of a diagnosed pathologic condition or disorder and 2) prophylactic or preventative measures that prevent and/or slow the development of a targeted pathologic condition or disorder. Thus those in need of treatment include those already with the disorder; those prone to have the disorder; and those in whom the disorder is to be prevented. Beneficial or desired clinical results include, but are not limited to, alleviation of symptoms, diminishment of extent of disease, stabilization (i.e., not worsening) of disease, delaying or slowing of disease progression, amelioration or palliation of the disease state, remission (whether partial or total), whether detectable or undetectable or any combination thereof. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, bears, and so on.

As used herein, phrases such as "a subject that would benefit from administration of an anti-SEMA4D antibody" and "an animal in need of treatment" includes subjects, such as mammalian subjects, that would benefit from administration of an anti-SEMA4D antibody or other SEMA4D binding molecule used, e.g., for detection of a SEMA4D polypeptide (e.g., for a diagnostic procedure) and/or from treatment, i.e., palliation or prevention of a disease, with an anti-SEMA4D antibody or other SEMA4D binding molecule.

A "binding molecule" or "antigen binding molecule" of the present invention refers in its broadest sense to a molecule that specifically binds an antigenic determinant. In one embodiment, the binding molecule specifically binds to SEMA4D, e.g., to a transmembrane SEMA4D polypeptide of about 150 kDa or a soluble SEMA4D polypeptide of about 120 kDa (commonly referred to as sSEMA4D). In another embodiment, a binding molecule of the invention is an antibody or an antigen binding fragment thereof. In another embodiment, a binding molecule of the invention comprises at least one heavy or light chain CDR of an antibody molecule. In another embodiment, a binding molecule of the invention comprises at least two CDRs from one or more antibody molecules. In another embodiment, a binding molecule of the invention comprises at least three CDRs from one or more antibody molecules. In another embodiment, a binding molecule of the invention comprises at least four CDRs from one or more antibody molecules. In another embodiment, a binding molecule of the invention comprises at least five CDRs from one or more antibody molecules. In another embodiment, a binding molecule of the invention comprises at least six CDRs from one or more antibody molecules.

The present invention is directed to a method of treating atherosclerosis, comprising administering to the subject an anti-SEMA4D binding molecule, e.g., an antibody, or antigen-binding fragment, variant, or derivative thereof. Unless specifically referring to full-sized antibodies such as naturally occurring antibodies, the term "anti-SEMA4D antibody" encompasses full-sized antibodies as well as antigen-binding fragments, variants, analogs, or derivatives of such antibodies, e.g., naturally occurring antibody or immunoglobulin molecules or engineered antibody molecules or fragments that bind antigen in a manner similar to antibody molecules.

As used herein, "human" or "fully human" antibodies include antibodies having the amino acid sequence of a human immunoglobulin and include antibodies isolated from human immunoglobulin libraries or from animals transgenic for one or more human immunoglobulins, as described above and, for example, in U.S. Pat. No. 5,939,598 by Kucherlapati et al. "Human" or "fully human" antibodies also include antibodies comprising at least the variable domain of a heavy chain, or at least the variable domains of a heavy chain and a light chain, where the variable domain(s) have the amino acid sequence of human immunoglobulin variable domain(s) or are humanized antibodies.

"Human" or "fully human" antibodies also include "human" or "fully human" antibodies, as described above, that comprise, consist essentially of, or consist of, variants (including derivatives) of antibody molecules (e.g., the VH regions and/or VL regions) described herein, which antibodies or fragments thereof immunospecifically bind to a SEMA4D polypeptide or fragment or variant thereof. Standard techniques known to those of skill in the art can be used to introduce mutations in the nucleotide sequence encoding a human anti-SEMA4D antibody, including, but not limited to, site-directed mutagenesis and PCR-mediated mutagenesis which result in amino acid substitutions. In some aspects, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH region, VHCDR1, VHCDR2, VHCDR3, VL region, VLCDR1, VLCDR2, or VLCDR3.

In certain embodiments, the amino acid substitutions are conservative amino acid substitution, discussed further below. Alternatively, mutations can be introduced randomly along all or part of the coding sequence, such as by saturation mutagenesis, and the resultant mutants can be screened for biological activity to identify mutants that retain activity (e.g., the ability to bind a SEMA4D polypeptide, e.g., human, murine, or both human and murine SEMA4D). Such variants (or derivatives thereof) of "human" or "fully human" antibodies can also be referred to as human or fully human antibodies that are "optimized" or "optimized for antigen binding" and include antibodies that have improved affinity to antigen.

The terms "antibody" and "immunoglobulin" are used interchangeably herein. An antibody or immunoglobulin comprises at least the variable domain of a heavy chain, and normally comprises at least the variable domains of a heavy chain and a light chain. Basic immunoglobulin structures in vertebrate systems are relatively well understood. See, e.g., Harlow et al. (1988) Antibodies: A Laboratory Manual (2nd ed.; Cold Spring Harbor Laboratory Press).

As used herein, the term "immunoglobulin" comprises various broad classes of polypeptides that can be distinguished biochemically. Those skilled in the art will appreciate that heavy chains are classified as gamma, mu, alpha, delta, or epsilon, (γ, μ, α, δ, ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the instant invention. All immunoglobulin classes are clearly within the scope of the present invention, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Light chains are classified as either kappa or lambda (κ, λ). Each heavy chain class can be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VL or VK) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the VL domain and VH domain, or subset of the complementarity determining regions (CDRs) within these variable domains, of an antibody combine to form the variable region that defines a three dimensional antigen binding site. This quaternary antibody structure forms the antigen binding site present at the end of each arm of the Y. More specifically, the antigen binding site is defined by three CDRs on each of the VH and VL chains. In some instances, e.g., certain immunoglobulin molecules derived from camelid species or engineered based on camelid immunoglobulins, a complete immunoglobulin molecule can consist of heavy chains only, with no light chains. See, e.g., Hamers-Casterman et al., *Nature* 363:446-448 (1993).

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a β-sheet conformation and the CDRs form loops that connect, and in some cases form part of, the β-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable domain by one of ordinary skill in the art, since they have been precisely defined (see below).

In the case where there are two or more definitions of a term that is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al. (1983) U.S. Dept. of Health and Human Services, "Sequences of Proteins of Immunological Interest" and by Chothia and Lesk, *J. Mol. Biol.* 196:901-917 (1987), which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues that encompass the CDRs as defined by each of the above cited references are set forth below in Table 1 as a comparison. The exact residue numbers that encompass a particular CDR will vary depending on the sequence and size of the CDR. Those skilled in the art can routinely determine which residues comprise a particular CDR given the variable region amino acid sequence of the antibody.

TABLE 1

CDR Definitions[1]

| | Kabat | Chothia |
|---|---|---|
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of all CDR definitions in Table 1 is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al. (1983) U.S. Dept. of Health and Human Services, "Sequence of Proteins of Immunological Interest." Unless otherwise specified, references to the numbering of specific amino acid residue positions in an anti-SEMA4D antibody or antigen-binding fragment, variant, or derivative thereof of the present invention are according to the Kabat numbering system.

Antibodies or antigen-binding fragments, variants, or derivatives thereof of the invention include, but are not limited to, polyclonal, monoclonal, multispecific and bispecific in which at least one arm is specific for SEMA4D, human, humanized, primatized, or chimeric antibodies, single-chain antibodies, epitope-binding fragments, e.g., Fab, Fab' and F(ab')$_2$, Fd, Fvs, single-chain Fvs (scFv), disulfide-linked Fvs (sdFv), fragments comprising either a VL or VH domain, fragments produced by a Fab expression library, and anti-idiotypic (anti-Id) antibodies (including, e.g., anti-Id antibodies to anti-SEMA4D antibodies disclosed herein). ScFv molecules are known in the art and are described, e.g., in U.S. Pat. No. 5,892,019. Immunoglobulin or antibody molecules of the invention can be of any type (e.g., IgG, IgE, IgM, IgD, IgA, and IgY), class (e.g., IgG1, IgG2, IgG3, IgG4, IgA1, and IgA2, etc.), or subclass of immunoglobulin molecule.

As used herein, the term "heavy chain portion" includes amino acid sequences derived from an immunoglobulin heavy chain. In certain embodiments, a polypeptide comprising a heavy chain portion comprises at least one of: a VH domain, a CH1 domain, a hinge (e.g., upper, middle, and/or lower hinge region) domain, a CH2 domain, a CH3 domain, or a variant or fragment thereof. For example, a binding polypeptide for use in the invention can comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the invention comprises a polypeptide chain comprising a CH3 domain. Further, a binding polypeptide for use in the invention can lack at least a portion of a CH2 domain (e.g., all or part of a CH2 domain). As set forth above, it will be understood by one of ordinary skill in the art that these domains (e.g., the heavy chain portions) can be modified such that they vary in amino acid sequence from the naturally occurring immunoglobulin molecule.

In certain anti-SEMA4D antibodies, or antigen-binding fragments, variants, or derivatives thereof disclosed herein, the heavy chain portions of one polypeptide chain of a multimer are identical to those on a second polypeptide chain of the multimer. Alternatively, heavy chain portion-containing monomers of the invention are not identical. For example, each monomer can comprise a different target binding site, forming, for example, a bispecific antibody.

The heavy chain portions of a binding molecule for use in the methods disclosed herein can be derived from different immunoglobulin molecules. For example, a heavy chain portion of a polypeptide can comprise a C$_{H1}$ domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain, e.g., a kappa or lambda light chain. In one aspect, the light chain portion comprises at least one of a VL or CL domain.

Anti-SEMA4D antibodies, or antigen-binding fragments, variants, or derivatives thereof disclosed herein can be described or specified in terms of the epitope(s) or portion(s) of an antigen, e.g., a target polypeptide disclosed herein (e.g., SEMA4D) that they recognize or specifically bind. The portion of a target polypeptide that specifically interacts with the antigen binding domain of an antibody is an "epitope," or an "antigenic determinant." A target polypeptide can comprise a single epitope, but typically comprises at least two epitopes, and can include any number of epitopes, depending on the size, conformation, and type of antigen. Furthermore, it should be noted that an "epitope" on a target polypeptide can be or can include non-polypeptide elements, e.g., an epitope can include a carbohydrate side chain.

The minimum size of a peptide or polypeptide epitope for an antibody is thought to be about four to five amino acids. Peptide or polypeptide epitopes can contain at least seven, at least nine, or between at least about 15 to about 30 amino acids. Since a CDR can recognize an antigenic peptide or polypeptide in its tertiary form, the amino acids comprising an epitope need not be contiguous, and in some cases, can be on two or more different peptide chain. A peptide or polypeptide epitope recognized by anti-SEMA4D antibodies of the present invention can contain a sequence of at least 4, at least 5, at least 6, at least 7, at least 8, at least 9, at least 10, at least 15, at least 20, at least 25, or between about 15 to about 30 contiguous or non-contiguous amino acids of SEMA4D.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" can be deemed to have a higher specificity for a given epitope than antibody "B," or antibody "A" can be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody that "preferentially binds" to a given epitope would more likely bind to that epitope than to a related epitope, even though such an antibody can cross-react with the related epitope.

By way of non-limiting example, an antibody can be considered to bind a first epitope preferentially if it binds the first epitope with a dissociation constant ($K_D$) that is less than the antibody's $K_D$ for the second epitope. In another non-limiting example, an antibody can be considered to bind a first antigen preferentially if it binds the first epitope with an affinity that is at least one order of magnitude less than the antibody's $K_D$ for the second epitope. In another non-limiting example, an antibody can be considered to bind a first epitope preferentially if it binds the first epitope with an affinity that is at least two orders of magnitude less than the antibody's $K_D$ for the second epitope.

In another non-limiting example, an antibody can be considered to bind a first epitope preferentially if it binds the first epitope with an off rate (k(off)) that is less than the antibody's k(off) for the second epitope. In another non-limiting example, an antibody can be considered to bind a first epitope preferentially if it binds the first epitope with an affinity that is at least one order of magnitude less than the antibody's k(off) for the second epitope. In another non-limiting example, an antibody can be considered to bind a first epitope preferentially if it binds the first epitope with an affinity that is at least two orders of magnitude less than the antibody's k(off) for the second epitope. An antibody or antigen-binding fragment, variant, or derivative disclosed herein can be said to bind a target polypeptide disclosed herein (e.g., SEMA4D, e.g., human, murine, or both human and murine SEMA4D) or a fragment or variant thereof with an off rate (k(off)) of less than or equal to $5\times10^{-2}$ $sec^{-1}$, $10^{-2}$ $sec^{-1}$, $5\times10^{-3}$ $sec^{-1}$ or $10^{-3}$ $sec^{-1}$. in certain aspects, an antibody of the invention can be said to bind a target polypeptide disclosed herein (e.g., SEMA4D, e.g., human, murine, or both human and murine SEMA4D) or a fragment or variant thereof with an off rate (k(off)) less than or equal to $5\times10^{-4}$ $sec^{-1}$, $10^{-4}$ $sec^{-1}$, $5\times10^{-5}$ $sec^{-1}$, or $10^{-5}$ $sec^{-1}$, $5\times10^{-6}$ $sec^{-1}$, $10^{-6}$ $sec^{-1}$, $5\times10^{-7}$ $sec^{-1}$ or $10^{-7}$ $sec^{-1}$.

An antibody or antigen-binding fragment, variant, or derivative disclosed herein can be said to bind a target polypeptide disclosed herein (e.g., SEMA4D, e.g., human, murine, or both human and murine SEMA4D) or a fragment or variant thereof with an on rate (k(on)) of greater than or equal to $10^3$ $M^{-1}$ $sec^{-1}$, $5\times10^3$ $M^{-1}$ $sec^{-1}$, $10^4$ $M^{-1}$ $sec^{-1}$, or $5\times10^4$ $M^{-1}$ $sec^{-1}$. In certain aspects, an antibody of the invention can be said to bind a target polypeptide disclosed herein (e.g., SEMA4D, e.g., human, murine, or both human and murine SEMA4D) or a fragment or variant thereof with an on rate (k(on)) greater than or equal to $10^5$ $M^{-1}$ $sec^{-1}$, $5\times10^5$ $M^{-1}$ $sec^{-1}$, $10^6$ $M^{-1}$ $sec^{-1}$, or $5\times10^6$ $M^{-1}$ $sec^{-1}$ or $10^7$ $M^{-1}$ $sec^{-1}$.

An antibody is said to competitively inhibit binding of a reference antibody to a given epitope if it preferentially binds to that epitope to the extent that it blocks, to some degree, binding of the reference antibody to the epitope. Competitive inhibition can be determined by any method known in the art, for example, competition ELISA assays. An antibody can be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of an immunoglobulin molecule. See, e.g., Harlow et al. (1988) Antibodies: A Laboratory Manual (Cold Spring Harbor Laboratory Press, 2nd ed.) pages 27-28. As used herein, the term "avidity" refers to the overall stability of the complex between a population of immunoglobulins and an antigen, that is, the functional combining strength of an immunoglobulin mixture with the antigen. See, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity.

Anti-SEMA4D antibodies or antigen-binding fragments, variants, or derivatives thereof of the invention can also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, can actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody can be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody can be deemed "highly specific" for a certain epitope, if it does not bind any other analog, ortholog, or homolog of that epitope.

Anti-SEMA4D binding molecules, e.g., antibodies or antigen-binding fragments, variants or derivatives thereof, of the invention can also be described or specified in terms of their binding affinity to a polypeptide of the invention, e.g., SEMA4D, e.g., human, murine, or both human and murine SEMA4D. Binding affinities can include those with a dissociation constant or Kd less than $5 \times 10^{-2}$ M, $10^{-2}$ M, $5 \times 10^{-3}$ M, $10^{-3}$ M, $5 \times 10^{4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M. In certain embodiments, the anti-SEMA4D binding molecule, e.g., an antibody or antigen binding fragment thereof, of the invention binds human SEMA4D with a Kd of about $5 \times 10^{-9}$ to about $6 \times 10^{-9}$. In another embodiment, the anti-SEMA4D binding molecule, e.g., an antibody or antigen binding fragment thereof, of the invention binds murine SEMA4D with a Kd of about $1 \times 10^{-9}$ to about $2 \times 10^{-9}$.

As used herein, the term "chimeric antibody" will be held to mean any antibody wherein the immunoreactive region or site is obtained or derived from a first species and the constant region (which can be intact, partial or modified in accordance with the instant invention) is obtained from a second species. In some embodiments the target binding region or site will be from a non-human source (e.g., mouse or primate) and the constant region is human.

As used herein, the term "engineered antibody" refers to an antibody in which the variable domain in either the heavy or light chain or both is altered by at least partial replacement of one or more CDRs from an antibody of known specificity and, if necessary, by partial framework region replacement and sequence changing. Although the CDRs can be derived from an antibody of the same class or even subclass as the antibody from which the framework regions are derived, it is envisaged that the CDRs will be derived from an antibody of different class, e.g., from an antibody from a different species. An engineered antibody in which one or more "donor" CDRs from a non-human antibody of known specificity is grafted into a human heavy or light chain framework region is referred to herein as a "humanized antibody." In certain embodiments, it is not necessary to replace all of the CDRs with the complete CDRs from the donor variable domain to transfer the antigen binding capacity of one variable domain to another. Rather, one can transfer just those residues needed to maintain the activity of the target binding site.

It is further recognized that the framework regions within the variable domain in a heavy or light chain, or both, of a humanized antibody can comprise solely residues of human origin, in which case these framework regions of the humanized antibody are referred to as "fully human framework regions" (for example, MAb VX15/2503, disclosed in U.S. Patent Appl. Publication No. US 2010/0285036 A1 as MAb 2503, incorporated herein by reference in its entirety). Alternatively, one or more residues of the framework region(s) of the donor variable domain can be engineered within the corresponding position of the human framework region(s) of a variable domain in a heavy or light chain, or both, of a humanized antibody if necessary to maintain proper binding or to enhance binding to the SEMA4D antigen. A human framework region that has been engineered in this manner would thus comprise a mixture of human and donor framework residues, and is referred to herein as a "partially human framework region."

For example, humanization of an anti-SEMA4D antibody can be essentially performed following the method of Winter and co-workers (Jones et al., Nature 321:522-525 (1986); Riechmann et al., Nature 332:323-327 (1988); Verhoeyen et al., Science 239:1534-1536 (1988)), by substituting rodent or mutant rodent CDRs or CDR sequences for the corresponding sequences of a human anti-SEMA4D antibody. See also U.S. Pat. Nos. 5,225,539; 5,585,089; 5,693,761; 5,693,762; 5,859,205; herein incorporated by reference. The resulting humanized anti-SEMA4D antibody would comprise at least one rodent or mutant rodent CDR within the fully human framework regions of the variable domain of the heavy and/or light chain of the humanized antibody. In some instances, residues within the framework regions of one or more variable domains of the humanized anti-SEMA4D antibody are replaced by corresponding non-human (for example, rodent) residues (see, for example, U.S. Pat. Nos. 5,585,089; 5,693,761; 5,693,762; and 6,180,370), in which case the resulting humanized anti-SEMA4D antibody would comprise partially human framework regions within the variable domain of the heavy and/or light chain.

Furthermore, humanized antibodies can comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the CDRs correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al., Nature 331:522-525 (1986); Riechmann et al., Nature 332:323-329 (1988); and Presta, Curr. Op. Struct. Biol. 2:593-596 (1992); herein incorporated by reference. Accordingly, such "humanized" antibodies can include antibodies wherein substantially less than an intact human variable domain has been substituted by the corresponding sequence from a non-human species. In practice, humanized antibodies are typically human antibodies in which some CDR residues and possibly some framework residues are substituted by residues from analogous sites in rodent antibodies. See, for example, U.S. Pat. Nos. 5,225,539; 5,585,089; 5,693,761; 5,693,762; 5,859,205. See also U.S. Pat. No. 6,180,370, and International Publication No. WO 01/27160, where humanized antibodies and techniques for producing humanized antibodies having improved affinity for a predetermined antigen are disclosed.

II. Target Polypeptide Description

As used herein, the terms "Semaphorin-4D," "SEMA4D" and "SEMA4D polypeptide" are used interchangeably, as are "SEMA4D" and "Sema4D." In certain embodiments, SEMA4D is expressed on the surface of or secreted by a cell. In another embodiment, SEMA4D is membrane bound. In another embodiments, SEMA4D is soluble, e.g., sSEMA4D. In other embodiments, SEMA4D can include a full-sized SEMA4D or a fragment thereof, or a SEMA4D variant polypeptide, wherein the fragment of SEMA4D or SEMA4D variant polypeptide retains some or all of the functional properties of the full-sized SEMA4D.

The full-sized human SEMA4D protein is a homodimeric transmembrane protein consisting of two polypeptide chains of 150 kDa. SEMA4D belongs to the semaphorin family of cell surface receptors and is also referred to as CD100. Both human and mouse SEMA4D/Sema4D are proteolytically cleaved from their transmembrane form to generate 120-kDa soluble forms, indicating the existence of two Sema4D isoforms (Kumanogoh et al., *J. Cell Science* 116(7):3464 (2003)). Semaphorins consist of soluble and membrane-bound proteins that were originally defined as axonal-guidance factors during development which play an important role in establishing precise connections between neurons and their appropriate target. Structurally considered a class IV semaphorin, SEMA4D consists of an amino-terminal signal sequence followed by a characteristic 'Sema' domain, which contains 17 conserved cysteine residues, an Ig-like domain, a lysine-rich stretch, a hydrophobic transmembrane region, and a cytoplasmic tail.

Each polypeptide chain of SEMA4D includes a signal sequence of about 13 amino acids followed by a semaphorin domain of about 512 amino acids, an immunoglobulin-like (Ig-like) domain of about 65 amino acids, a lysine-rich stretch of 104 amino acids, a hydrophobic transmembrane region of about 19 amino acids, and a cytoplasmic tail of 110 amino acids. A consensus site for tyrosine phosphorylation in the cytoplasmic tail supports the predicted association of SEMA4D with a tyrosine kinase (Schlossman, et al., Eds. (1995) Leucocyte Typing V (Oxford University Press, Oxford).

SEMA4D is known to have at least three functional receptors, Plexin-B1, Plexin-B2 and CD72. One of the receptors, Plexin-B1, is expressed in non-lymphoid tissues and has been shown to be a high affinity (1 nM) receptor for SEMA4D (Tamagnone et al., *Cell* 99:71-80 (1999)). SEMA4D stimulation of Plexin-B1 signaling has been shown to induce growth cone collapse of neurons, and to induce process extension collapse and apoptosis of oligodendrocytes (Giraudon et al., *J. Immunol.* 172:1246-1255 (2004); Giraudon et al., *NeuroMolecular Med.* 7:207-216 (2005)). After binding to SEMA4D, Plexin-B1 signaling mediates the inactivation of R-Ras, leading to a decrease in the integrin mediated attachment to the extracellular matrix, as well as to activation of RhoA, leading to reorganization of the cytoskeleton and cell migration. See Kruger et al., *Nature Rev. Mol. Cell Biol.* 6:789-800 (2005); Pasterkamp, *TRENDS in Cell Biology* 15:61-64 (2005)). Plexin-B2, on the other hand, has an intermediate affinity for SEMA4D and a recent report indicates that Plexin-B2 is expressed on keratinocytes and activates SEMA4D-positive γδ T cells to contribute to epithelial repair (Witherden et al., *Immunity.* 2012 Aug. 24; 37(2):314-25).

In lymphoid tissues CD72 is utilized as a low affinity (300 nM) SEMA4D receptor (Kumanogoh et al., *Immunity* 13:621-631 (2000)). B cells and APCs express CD72, and anti-CD72 antibodies have many of the same effects as sSEMA4D, such as enhancement of CD40-induced B cell responses and B cell shedding of CD23. CD72 is thought to act as a negative regulator of B cell responses by recruiting the tyrosine phosphatase SHP-1, which can associate with many inhibitory receptors. Interaction of SEMA4D with CD72 results in the dissociation of SHP-1, and the loss of this negative activation signal. SEMA4D has been shown to promote T cell stimulation and B cell aggregation and survival in vitro. The addition of SEMA4D-expressing cells or sSEMA4D enhances CD40-induced B cell proliferation and immunoglobulin production in vitro, and accelerates in vivo antibody responses (Ishida et al., *Inter. Immunol.* 15:1027-1034 (2003); Kumanogoh and H. Kukutani, *Trends in Immunol.* 22:670-676 (2001)). sSEMA4D enhances the CD40 induced maturation of DCs, including up-regulation of costimulatory molecules and increased secretion of IL-12. In addition, sSEMA4D can inhibit immune cell migration, which can be reversed by addition of blocking anti-SEMA4D antibodies (Elhabazi et al., *J. Immunol.* 166:4341-4347 (2001); Delaire et al., *J. Immunol.* 166:4348-4354 (2001)).

Sema4D is expressed at high levels in lymphoid organs, including the spleen, thymus, and lymph nodes, and in non-lymphoid organs, such as the brain, heart, and kidney. In lymphoid organs, Sema4D is abundantly expressed on resting T cells but only weakly expressed on resting B cells and antigen-presenting cells (APCs), such as dendritic cells (DCs). Cellular activation increases the surface expression of SEMA4D as well as the generation of soluble SEMA4D (sSEMA4D).

The expression pattern of SEMA4D suggests that it plays an important physiological as well as pathological role in the immune system. SEMA4D has been shown to promote B cell activation, aggregation and survival; enhance CD40-induced proliferation and antibody production; enhance antibody response to T cell dependent antigens; increase T cell proliferation; enhance dendritic cell maturation and ability to stimulate T cells; and is directly implicated in demyelination and axonal degeneration (Shi et al., *Immunity* 13:633-642 (2000); Kumanogoh et al., *J Immunol* 169:1175-1181 (2002); and Watanabe et al., *J Immunol* 167:4321-4328 (2001)).

SEMA4D knock out (SEMA4D−/−) mice have provided additional evidence that SEMA4D plays an important role in both humoral and cellular immune responses. There are no known major abnormalities of non-lymphoid tissues in SEMA4D−/− mice. Dendritic cells (DCs) from the SEMA4D−/− mice have poor allostimulatory ability and show defects in expression of costimulatory molecules, which can be rescued by the addition of sSEMA4D. Mice deficient in SEMA4D (SEMA4D−/−) fail to develop experimental autoimmune encephalomyelitis induced by myelin oligodendrocyte glycoprotein peptide, because myelin oligodendrocyte glycoprotein-specific T cells are poorly generated in the absence of SEMA4D (Kumanogoh et al., *J Immunol* 169:1175-1181 (2002)). A significant amount of soluble SEMA4D is also detected in the sera of autoimmunity-prone MRL/lpr mice (model of systemic autoimmune diseases such as SLE), but not in normal mice. Further, the levels of sSEMA4D correlate with levels of auto-antibodies and increase with age (Wang et al., *Blood* 97:3498-3504 (2001)). Soluble SEMA4D has also been shown to accumulate in the cerebral spinal fluid and sera of patients with demyelinating disease, and sSEMA4D induces apoptosis of human pluripotent neural precursors (Dev cells), and both inhibits process extension and induces apoptosis of rat oligodendrocytes in vitro (Giraudon et al., *J Immunol* 172 (2):1246-1255 (2004)). This apoptosis was blocked by an anti-SEMA4D MAb.

III. Anti-SEMA4D Antibodies

Antibodies that bind SEMA4D have been described in the art. See, for example, US Publ. Nos. 2008/0219971 A1, US 2010/0285036 A1, and US 2006/0233793 A1, International Patent Applications WO 93/14125, WO 2008/100995, and WO 2010/129917, and Herold et al., *Int. Immunol.* 7(1): 1-8 (1995), each of which is herein incorporated in its entirety by reference.

This disclosure generally relates to a method of treating atherosclerosis in a subject having an inflammatory disorder, e.g., a human patient, comprising administration of an antibody which specifically binds to SEMA4D, or an antigen-binding fragment, variant, or derivative thereof. In certain embodiments, the antibody blocks the interaction of SEMA4D with one or more of its receptors, e.g., Plexin-B1. Anti-SEMA4D antibodies having these properties can be used in the methods provided herein. Antibodies that can be used include, but are not limited to MAbs VX15/2503, 67, and 76 and antigen-binding fragments, variants, or derivatives thereof which are fully described in US 2010/0285036 A1. Additional antibodies which can be used in the methods provided herein include the BD16 and BB 18 antibodies described in US 2006/0233793 A1 as well as antigen-binding fragments, variants, or derivatives thereof; or any of MAb 301, MAb 1893, MAb 657, MAb 1807, MAb 1656, MAb 1808, Mab 59, MAb 2191, MAb 2274, MAb 2275, MAb 2276, MAb 2277, MAb 2278, MAb 2279, MAb 2280, MAb 2281, MAb 2282, MAb 2283, MAb 2284, and MAb 2285, as well as any fragments, variants or derivatives thereof as described in US 2008/0219971 A1. In certain embodiments an anti-SEMA4D antibody for use in the methods provided herein binds human, murine, or both human and murine SEMA4D. Also useful are antibodies which bind to the same epitope as any of the aforementioned antibodies and/or antibodies which competitively inhibit any of the aforementioned antibodies.

In certain embodiments, an anti-SEMA4D antibody or antigen-binding fragment, variant, or derivative thereof useful in the methods provided herein has an amino acid sequence that has at least about 80%, about 85%, about 88%, about 89%, about 90%, about 91%, about 92%, about 93%, about 94%, or about 95% sequence identity to the amino acid sequence for a reference anti-SEMA4D antibody molecule, for example those described above. In a further embodiment, the binding molecule shares at least about 96%, about 97%, about 98%, about 99%, or 100% sequence identity to a reference antibody.

In another embodiment, an anti-SEMA4D antibody or antigen-binding fragment, variant, or derivative thereof useful in the methods provided herein comprises, consists essentially of, or consists of an immunoglobulin heavy chain variable domain (VH domain), where at least one of the CDRs of the VH domain has an amino acid sequence that is at least about 80%, about 85%, about 90%, about 95%, about 96%, about 97%, about 98%, about 99%, or identical to CDR1, CDR2 or CDR3 of SEQ ID NO: 9 or 10.

In another embodiment, an anti-SEMA4D antibody or antigen-binding fragment, variant, or derivative thereof useful in the methods provided herein comprises, consists essentially of, or consists of an immunoglobulin heavy chain variable domain (VH domain), where at least one of the CDRs of the VH domain has an amino acid sequence that is at least about 80%, about 85%, about 90%, about 95%, about 96%, about 97%, about 98%, about 99%, or identical to SEQ ID NO: 6, SEQ ID NO: 7, or SEQ ID NO: 8.

In another embodiment, an anti-SEMA4D antibody or antigen-binding fragment, variant, or derivative thereof useful in the methods provided herein comprises, consists essentially of, or consists of an immunoglobulin heavy chain variable domain (VH domain), where at least one of the CDRs of the VH domain has an amino acid sequence identical, except for 1, 2, 3, 4, or 5 conservative amino acid substitutions, to SEQ ID NO: 6, SEQ ID NO: 7, or SEQ ID NO: 8.

In another embodiment, an anti-SEMA4D antibody or antigen-binding fragment, variant, or derivative thereof useful in the methods provided herein comprises, consists essentially of, or consists of a VH domain that has an amino acid sequence that is at least about 80%, about 85%, about 90%, about 91%, about 92%, about 93%, about 94%, about 95%, about 96%, about 97%, about 98%, about 99%, or 100% identical to SEQ ID NO: 9 or SEQ ID NO: 10, wherein an anti-SEMA4D antibody comprising the encoded VH domain specifically or preferentially binds to SEMA4D.

In another embodiment, an anti-SEMA4D antibody or antigen-binding fragment, variant, or derivative thereof useful in the methods provided herein comprises, consists essentially of, or consists of an immunoglobulin light chain variable domain (VL domain), where at least one of the CDRs of the VL domain has an amino acid sequence that is at least about 80%, about 85%, about 90%, about 95%, about 96%, about 97%, about 98%, about 99%, or identical to CDR1, CDR2 or CDR3 of SEQ ID NO: 17 or 18.

In another embodiment, an anti-SEMA4D antibody or antigen-binding fragment, variant, or derivative thereof useful in the methods provided herein comprises, consists essentially of, or consists of an immunoglobulin light chain variable domain (VL domain), where at least one of the CDRs of the VL domain has an amino acid sequence that is at least about 80%, about 85%, about 90%, about 95%, about 96%, about 97%, about 98%, about 99%, or identical to SEQ ID NO: 14, SEQ ID NO: 15, or SEQ ID NO: 16.

In another embodiment, an anti-SEMA4D antibody or antigen-binding fragment, variant, or derivative thereof useful in the methods provided herein comprises, consists essentially of, or consists of an immunoglobulin light chain variable domain (VL domain), where at least one of the CDRs of the VL domain has an amino acid sequence identical, except for 1, 2, 3, 4, or 5 conservative amino acid substitutions, to SEQ ID NO: 14, SEQ ID NO: 15, or SEQ ID NO: 16.

In a further embodiment, an anti-SEMA4D antibody or antigen-binding fragment, variant, or derivative thereof useful in the methods provided herein comprises, consists essentially of, or consists of a VL domain that has an amino acid sequence that is at least about 80%, about 85%, about 90%, about 91%, about 92%, about 93%, about 94%, about 95%, about 96%, about 97%, about 98%, about 99%, or 100% identical to SEQ ID NO: 17 or SEQ ID NO: 18, wherein an anti-SEMA4D antibody comprising the encoded VL domain specifically or preferentially binds to SEMA4D.

Also included for use in the methods provided herein are polypeptides encoding anti-SEMA4D antibodies, or antigen-binding fragments, variants, or derivatives thereof as described herein, polynucleotides encoding such polypeptides, vectors comprising such polynucleotides, and host cells comprising such vectors or polynucleotides, all for producing anti-SEMA4D antibodies, or antigen-binding fragments, variants, or derivatives thereof for use in the methods described herein.

Suitable biologically active variants of the anti-SEMA4D antibodies of the invention can be used in the methods of the present invention. Such variants will retain the desired binding properties of the parent anti-SEMA4D antibody. Methods for making antibody variants are generally available in the art.

Methods for mutagenesis and nucleotide sequence alterations are well known in the art. See, for example, Walker and Gaastra, eds. (1983) *Techniques in Molecular Biology* (MacMillan Publishing Company, New York); Kunkel, *Proc. Natl. Acad. Sci. USA* 82:488-492 (1985); Kunkel et al., *Methods Enzymol.* 154:367-382 (1987); Sambrook et al. (1989) *Molecular Cloning: A Laboratory Manual* (Cold Spring Harbor, N.Y.); U.S. Pat. No. 4,873,192; and the references cited therein; herein incorporated by reference. Guidance as to appropriate amino acid substitutions that do not affect biological activity of the polypeptide of interest can be found in the model of Dayhoff et al. (1978) in *Atlas of Protein Sequence and Structure* (Natl. Biomed. Res. Found., Washington, D.C.), pp. 345-352, herein incorporated by reference in its entirety. The model of Dayhoff et al. uses the Point Accepted Mutation (PAM) amino acid similarity matrix (PAM 250 matrix) to determine suitable conservative amino acid substitutions. In some aspects amino acid substitutions can be conservative substitutions, such as exchanging one amino acid with another having similar properties. Examples of conservative amino acid substitutions as taught by the PAM 250 matrix of the Dayhoff et al. model include, but are not limited to, Gly↔Ala, Val↔Ile ↔Leu, Asp↔Glu, Lys↔Arg, Asn↔Gln, and Phe↔Trp ↔Tyr.

In constructing variants of the anti-SEMA4D binding molecule, e.g., an antibody or antigen-binding fragment thereof, polypeptides of interest, modifications are made such that variants continue to possess the desired properties, e.g., being capable of specifically binding to a SEMA4D, e.g., human, murine, or both human and murine SEMA4D, e.g., expressed on the surface of or secreted by a cell and having SEMA4D blocking activity, as described herein. Mutations made in the DNA encoding the variant polypeptide should not place the sequence out of reading frame and in certain aspects will not create complementary regions that could produce secondary mRNA structure. See EP Patent Application Publication No. 75,444.

Methods for measuring anti-SEMA4D binding molecule, e.g., an antibody or antigen-binding fragment, variant, or derivative thereof, binding specificity include, but are not limited to, standard competitive binding assays, assays for monitoring immunoglobulin secretion by T cells or B cells, T cell proliferation assays, apoptosis assays, ELISA assays, and the like. See, for example, such assays disclosed in WO 93/14125; Shi et al., *Immunity* 13:633-642 (2000); Kumanogoh et al., *J Immunol* 169:1175-1181 (2002); Watanabe et al., *J Immunol* 167:4321-4328 (2001); Wang et al., *Blood* 97:3498-3504 (2001); and Giraudon et al., *J Immunol* 172(2):1246-1255 (2004), all of which are herein incorporated by reference.

When discussed herein whether any particular polypeptide, including the constant regions, CDRs, VH domains, or VL domains disclosed herein, is at least about 65%, about 70%, about 75%, about 80%, about 85%, about 90%, about 91%, about 92%, about 93%, about 94%, about 95%, about 96%, about 97%, about 98%, about 99%, or even about 100% identical to another polypeptide, the % identity can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman (1981) Adv. Appl. Math. 2:482-489, to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of amino acids in the reference sequence are allowed.

For purposes of the present invention, percent sequence identity can be determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman (1981) Adv. Appl. Math. 2:482-489. A variant can, for example, differ from a reference anti-SEMA4D antibody (e.g., MAb VX15/2503, 67 or 76) by as few as 1 to 15 amino acid residues, as few as 1 to 10 amino acid residues, such as 6-10, as few as 5, as few as 4, 3, 2, or even 1 amino acid residue.

Percentage of "sequence identity" can also be determined by comparing two optimally aligned sequences over a comparison window. In order to optimally align sequences for comparison, the portion of a polynucleotide or polypeptide sequence in the comparison window can comprise additions or deletions termed gaps while the reference sequence is kept constant. An optimal alignment is that alignment which, even with gaps, produces the greatest possible number of "identical" positions between the reference and comparator sequences. Percentage "sequence identity" between two sequences can be determined using the version of the program "BLAST 2 Sequences" which was available from the National Center for Biotechnology Information as of Sep. 1, 2004, which program incorporates the programs BLASTN (for nucleotide sequence comparison) and BLASTP (for polypeptide sequence comparison), which programs are based on the algorithm of Karlin and Altschul (*Proc. Natl. Acad. Sci. USA* 90(12):5873-5877, 1993). When utilizing "BLAST 2 Sequences," parameters that were default parameters as of Sep. 1, 2004, can be used for word size (3), open gap penalty (11), extension gap penalty (1), gap drop-off (50), expect value (10) and any other required parameter including but not limited to matrix option.

The constant region of an anti-SEMA4D antibody can be mutated to alter effector function in a number of ways. For example, see U.S. Pat. No. 6,737,056B1 and U.S. Patent Application Publication No. 2004/0132101A1, which disclose Fc mutations that optimize antibody binding to Fc receptors.

In certain anti-SEMA4D antibodies or fragments, variants or derivatives thereof useful in the methods provided herein, the Fc portion can be mutated to decrease effector function using techniques known in the art. For example, the deletion or inactivation (through point mutations or other means) of a constant region domain can reduce Fc receptor binding of the circulating modified antibody thereby increasing tumor localization. In other cases, constant region modifications consistent with the instant invention moderate complement binding and thus reduce the serum half-life. Yet other modifications of the constant region can be used to modify disulfide linkages or oligosaccharide moieties that allow for enhanced localization due to increased antigen specificity or antibody flexibility. The resulting physiological profile, bioavailability and other biochemical effects of the modifications, such as tumor localization, biodistribution and serum half-life, can easily be measured and quantified using well known immunological techniques without undue experimentation. Anti-SEMA4D antibodies for use in the methods provided herein include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, etc. Additionally, the derivative can contain one or more non-classical amino acids.

A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind an anti-SEMA4D polypeptide, to block SEMA4D interaction with its receptor, or to reduce, inhibit, suppress and/or delay plaque formation in a subject, e.g., a patient with an inflammatory disorder or atherosclerosis).

For example, it is possible to introduce mutations only in framework regions or only in CDR regions of an antibody molecule. Introduced mutations can be silent or neutral missense mutations, i.e., have no, or little, effect on an antibody's ability to bind antigen. These types of mutations can be useful to optimize codon usage, or improve a hybridoma's antibody production. Alternatively, don-neutral missense mutations can alter an antibody's ability to bind antigen. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein can routinely be expressed and the functional and/or biological activity of the encoded protein, (e.g., ability to immunospecifically bind at least one epitope of a SEMA4D polypeptide) can be determined using techniques described herein or by routinely modifying techniques known in the art.

In certain embodiments, the anti-SEMA4D antibodies for use in the methods provided herein comprise at least one optimized complementarity-determining region (CDR). By "optimized CDR" is intended that the CDR has been modified and optimized to improve binding affinity and/or anti-SEMA4D activity that is imparted to an anti-SEMA4D antibody comprising the optimized CDR. "Anti-SEMA4D activity" or "SEMA4D blocking activity" can include activity which modulates one or more of the following activities associated with SEMA4D: B cell activation, aggregation and survival; CD40-induced proliferation and antibody production; antibody response to T cell dependent antigens; T cell or other immune cell proliferation; dendritic cell maturation; demyelination and axonal degeneration; apoptosis of pluripotent neural precursors and/or oligodendrocytes; induction of endothelial cell migration; inhibition of spontaneous monocyte migration; binding to cell surface Plexin-B1 or other receptor, or any other activity associated with soluble SEMA4D or SEMA4D that is expressed on the surface of SEMA4D+ cells. Anti-SEMA4D activity can also be attributed to a decrease in incidence or severity of diseases associated with SEMA4D expression, including, but not limited to, certain types of cancers including lymphomas, autoimmune diseases, inflammatory diseases including central nervous system (CNS) and peripheral nervous system (PNS) inflammatory diseases, transplant rejections, and invasive angiogenesis. Examples of optimized antibodies based on murine anti-SEMA4D MAbs BD16 and BB 18, were described in US Publ. No. 2008/0219971 A1, International Patent Application WO 93/14125 and Herold et al., *Int. Immunol.* 7(1): 1-8 (1995), each of which are herein incorporated by reference in their entirety. The modifications can involve replacement of amino acid residues within the CDR such that an anti-SEMA4D antibody retains specificity for the SEMA4D antigen and has improved binding affinity and/or improved anti-SEMA4D activity.

IV. Treatment Methods Using Therapeutic Anti-SEMA4D Antibodies

Methods of the invention are directed to the use of anti-SEMA4D binding molecules, e.g., antibodies, including antigen-binding fragments, variants, and derivatives thereof, to treat atherosclerosis in a subject having atherosclerosis. In certain embodiments the endothelial cells express a SEMA4D receptor, in certain embodiments the receptor is Plexin-B1. Though the following discussion refers to administration of an anti-SEMA4D antibody, the methods described herein are also applicable to the antigen-binding fragments, variants, and derivatives of these anti-SEMA4D antibodies that retain the desired properties of the anti-SEMA4D antibodies of the invention, e.g., capable of specifically binding SEMA4D, e.g., human, mouse, or human and mouse SEMA4D, having SEMA4D neutralizing activity, and/or blocking the interaction of SEMA-4D with its receptor, e.g., Plexin-B1. The methods described herein are also applicable to other biologic products or small molecule drugs that retain the desired properties of the antibodies of the invention, e.g., capable of specifically binding SEMA4D, e.g., human, mouse, or human and mouse SEMA4D, having SEMA4D neutralizing activity, and/or blocking the interaction of SEMA4D with its receptors.

In one embodiment, treatment includes the application or administration of an anti-SEMA4D binding molecule, e.g., an antibody or antigen binding fragment thereof as described herein to a patient, where the patient has, or has the risk of developing a coronary artery disease. In another embodiment, treatment is also intended to include the application or administration of a pharmaceutical composition comprising the anti-SEMA4D binding molecule, e.g., an antibody or antigen binding fragment thereof to a patient, where the patient has, or has the risk of developing a coronary artery disease.

The anti-SEMA4D binding molecules, e.g., antibodies or binding fragments thereof as described herein are useful for the treatment of inflammatory diseases, including atherosclerosis. In some embodiments, treatment of atherosclerosis can reduce, inhibit, suppress and/or delay the formation of atherosclerotic plaques and/or reduce, inhibit, suppress and/or delay the growth of atherosclerotic plaques. Atherosclerotic plaques are build-ups of fat, cholesterol, calcium, and other substances found in the blood that harden and narrow the arteries over time, thereby limiting the flow of oxygen-rich blood to organs and other parts of the body.

In other embodiments, treatment of atherosclerosis can reduce or decrease neovascularization that occurs in or around atherosclerotic plaques. Neovascularization occurs in the atherosclerotic plaques of human aorta and coronary arteries (Carmeliet P, *Nature Med* 9: 653-660, 2003; and Zhang Y et al., *Am J Pathol* 143: 164-172, 1993). These neovessels are originally derived from the adventitial vasa vasorum and serve to nourish thickened atherosclerotic intimal growth (Kumamoto M et al., *Hum Pathol* 26: 450-456, 1995). Thus, neovascularization is a major cause of atherosclerotic plaque growth and destabilization (Barger A C et al., *N Engl J Med* 310: 175-177, 1984). Several studies explore the mechanism by which neovascularization facilitates atheroma formation (Moreno P R et al., *Circulation* 113: 2245-2252, 2006; and Cheng X W et al., *Hypertension* 57:981-989, 2011). Since the vasa vasorum density highly correlates with the number of inflammatory mononuclear cells infiltrating into the plaque, new vessel formation in the plaque is considered to provide crucial entry sites for leukocyte migration into atherosclerotic plaque (O'Brien E R et al., *Am J Pathol* 145: 883-894, 1994; and Moulton K S et al., *Proc Natl Acad Sci USA* 100: 4736-4741, 2003). Hemorrhage from plaque neovessels further enlarges the plaque size by helping blood lipid deposit in the lipid core of atheroma (Kolodgie F D et al., *N Engl J Med* 349: 2316-25, 2003). Angiogenesis inhibitors including angiostatin or TNP-4570 have been shown to suppress plaque growth by decreasing new vessel formation in atherosclerosis-prone apolipoprotein E-deficient (ApoE−/−) mice, which indicates the functional importance of neovascularization in the progression of atherosclerosis (Moulton K S et al., *Proc Natl Acad Sci USA* 100: 4736-4741, 2003; and Moulton K S et al., *Circulation* 99: 1726-32, 1999). Furthermore, neovessels formed in atherosclerotic plaque can exacerbate atherosclerosis by increasing the amount of metalloproteinase secreted into the plaque from blood, and finally inducing plaque rupture and thrombus formation (Jonsson-Rylander A C et al., *Arterioscler Thromb Vasc Biol* 25: 180-185, 2005.).

In other embodiments, the anti-SEMA4D binding molecules, e.g., antibodies or binding fragments thereof as described herein can be useful for the treatment of other inflammatory diseases. Examples of such diseases can include, but are not limited to, cardiovascular diseases, rheumatoid arthritis, gastroenterological diseases, neuroinflammatory diseases (e.g., multiple sclerosis), and even certain types of cancer (e.g., gallbladder carcinoma).

In one embodiment, the invention relates to the use of anti-SEMA4D binding molecules, e.g., antibodies or antigen-binding fragments, variants, or derivatives thereof, as a medicament, in particular for use in the treatment or prophylaxis of atherosclerosis to inhibit, reduce, prevent, minimize, and/or delay the formation of atherosclerotic plaques and/or inhibit, reduce, prevent, minimize, and/or delay the neovascularization in the atherosclerotic plaques.

In accordance with the methods of the present invention, at least one anti-SEMA4D binding molecule, e.g., an antibody or antigen binding fragment, variant, or derivative thereof, as defined elsewhere herein can be used to promote a positive therapeutic response with respect to atherosclerosis. A "positive therapeutic response" with respect to atherosclerosis is intended to include an improvement in the disease in association with plaque formation, plaque neovascularization, plaque growth, and/or an improvement in the symptoms associated with the disease. That is, delayed atherosclerotic plaque formation, reduced neovascularization of the plaques, reduced inflammation, decreased growth of the plaques, combinations thereof, and the like, can be observed. Such positive therapeutic responses are not limited to the route of administration and can comprise administration to the donor, the donor tissue (such as for example organ perfusion), the host, any combination thereof, and the like. In particular, the methods provided herein are directed to inhibiting, preventing, reducing, alleviating, or lessening the development of atherosclerosis in a patient. Thus, for example, an improvement in the disease can be characterized as an absence of clinically observable symptoms, a reduction, inhibition, suppression and/or delay in plaque formation or plaque growth, a reduction, inhibition, suppression and/or delay in neovascularization, a reduction in inflammation, or a change in the morphology or function of the plaques.

The anti-SEMA4D binding molecules, e.g., antibodies or antigen binding fragments, variants, or derivatives thereof can be used in combination with at least one or more other treatments for atherosclerosis; where the additional therapy is administered prior to, during, or subsequent to the anti-SEMA4D binding molecule, e.g., antibody or antigen binding fragment, variant, or derivative thereof, therapy. Thus, where the combined therapies comprise administration of an anti-SEMA4D binding molecule, e.g., an antibody or antigen binding fragment, variant, or derivative thereof, in combination with administration of another therapeutic agent, the methods of the invention encompass coadministration, using separate formulations or a single pharmaceutical formulation, with simultaneous or consecutive administration in either order.

To apply the methods and systems of the disclosure in certain embodiments, samples or images from a patient can be obtained before, after, or both before and after the administration of a therapy comprising either: (1) an effective amount of an isolated binding molecule that specifically binds to Semaphorin-4D (SEMA4D); or (2) an effective amount of an isolated binding molecule that specifically binds to Semaphorin-4D (SEMA4D) to a subject having atherosclerosis or inflammatory disease. In some cases, successive samples or images can be obtained from the patient after therapy has commenced, after therapy has ceased, or both before and after therapy. Samples or images can, for example, be requested by a healthcare provider (e.g., a doctor) or healthcare benefits provider, obtained and/or processed by the same or a different healthcare provider (e.g., a nurse, a hospital) or a clinical laboratory, and after processing, the results can be forwarded to yet another healthcare provider, healthcare benefits provider, or the patient. Similarly, the measuring/determination of one or more scores, comparisons between scores, evaluation of the scores and treatment decisions can be performed by one or more healthcare providers, healthcare benefits providers, and/or clinical laboratories.

As used herein, the term "healthcare provider" refers to individuals or institutions that directly interact and administer to living subjects, e.g., human patients. Non-limiting examples of healthcare providers include doctors, nurses, technicians, therapist, pharmacists, counselors, alternative medicine practitioners, medical facilities, doctor's offices, hospitals, emergency rooms, clinics, urgent care centers, alternative medicine clinics/facilities, and any other entity providing general and/or specialized treatment, assessment, maintenance, therapy, medication, and/or advice relating to all, or any portion of, a patient's state of health, including but not limited to general medical, specialized medical, surgical, and/or any other type of treatment, assessment, maintenance, therapy, medication and/or advice.

In some aspects, a healthcare provider can administer or instruct another healthcare provider to administer a therapy comprising either: (1) an effective amount of an isolated binding molecule that specifically binds to Semaphorin-4D (SEMA4D); or (2) an effective amount of an isolated binding molecule that specifically binds to Semaphorin-4D (SEMA4D), where the subject has, or is suspected to have, atherosclerosis or inflammatory disease. A healthcare provider can implement or instruct another healthcare provider or patient to perform the following actions: obtain a sample or image, process a sample or image, submit a sample or image, receive a sample or image, transfer a sample or image, analyze or measure a sample or image, quantify a sample or image, provide the results obtained after analyzing/measuring/quantifying a sample or image, receive the results obtained after analyzing/measuring/quantifying a sample or image, compare/score the results obtained after analyzing/measuring/quantifying one or more samples or images, provide the comparison/score from one or more samples, obtain the comparison/score from one or more samples or images, administer a therapy (e.g., (1) an effective amount of an isolated binding molecule that specifically binds to Semaphorin-4D (SEMA4D); or (2) an effective amount of an isolated binding molecule that specifically binds to Semaphorin-4D (SEMA4D) to a subject, where the subject has, or is suspected to have, atherosclerosis or inflammatory disease, commence the administration of a therapy, cease the administration of a therapy, continue the administration of a therapy, temporarily interrupt the administration of a therapy, increase the amount of an administered therapeutic agent, decrease the amount of an administered therapeutic agent, continue the administration of an amount of a therapeutic agent, increase the frequency of administration of a therapeutic agent, decrease the frequency of administration of a therapeutic agent, maintain the same dosing frequency on a therapeutic agent, replace a therapy or therapeutic agent by at least another therapy or therapeutic agent, combine a therapy or therapeutic agent with at least another therapy or additional therapeutic agent.

In some aspects, a healthcare benefits provider can authorize or deny, for example, collection of a sample or image, processing of a sample or image, submission of a sample or image, receipt of a sample or image, transfer of a sample or image, analysis or measurement a sample or image, quantification a sample or image, provision of results obtained after analyzing/measuring/quantifying a sample or image, transfer of results obtained after analyzing/measuring/quantifying a sample or image, comparison/scoring of results obtained after analyzing/measuring/quantifying one or more samples or images, transfer of the comparison/score from one or more samples or images, administration of a therapy or therapeutic agent, commencement of the administration of a therapy or therapeutic agent, cessation of the administration of a therapy or therapeutic agent, continuation of the administration of a therapy or therapeutic agent, temporary interruption of the administration of a therapy or therapeutic agent, increase of the amount of administered therapeutic agent, decrease of the amount of administered therapeutic agent, continuation of the administration of an amount of a therapeutic agent, increase in the frequency of administration of a therapeutic agent, decrease in the frequency of administration of a therapeutic agent, maintain the same dosing frequency on a therapeutic agent, replace a therapy or therapeutic agent by at least another therapy or therapeutic agent, or combine a therapy or therapeutic agent with at least another therapy or additional therapeutic agent.

In addition, a healthcare benefits provider can, e.g., authorize or deny the prescription of a therapy, authorize or deny coverage for therapy, authorize or deny reimbursement for the cost of therapy, determine or deny eligibility for therapy, etc.

In some aspects, a clinical laboratory can, for example, collect or obtain a sample, process a sample, submit a sample, receive a sample, transfer a sample, analyze or measure a sample, quantify a sample, provide the results obtained after analyzing/measuring/quantifying a sample, receive the results obtained after analyzing/measuring/quantifying a sample, compare/score the results obtained after analyzing/measuring/quantifying one or more samples, provide the comparison/score from one or more samples, obtain the comparison/score from one or more samples, or other related activities.

In some aspects, a healthcare provider, clinical laboratory, or other entity can, for example, collect or obtain an image, process an image, submit an image, receive an image, transfer an image, analyze or measure an image, quantify an image, provide the results obtained after analyzing/measuring/quantifying an image, receive the results obtained after analyzing/measuring/quantifying an image, compare/score the results obtained after analyzing/measuring/quantifying one or more images, provide the comparison/score from one or more images, obtain the comparison/score from one or more images, or other related activities. Images that can be used in such aspects include, but are not limited to, images obtained by coronary angiography, intravascular ultrasound (IVUS), carotid ultrasound, coronary computed tomography (CT), magnetic resonance imaging (MRI), positron emission tomography (PET), optical coherence tomography (OCT), near-infrared spectroscopy (NIRS), and NIR fluorescence. In certain embodiments, imaging techniques that have been described in the literature can be used (Tardif et al. *Circ Cardiovasc Imaging* 4:319-333 (2011)).

VII. Methods of Diagnosis and Treatment

In certain embodiments, this disclosure provides methods of treating a subject, e.g., a patient having atherosclerosis, where the subject has elevated levels of either B cells, T cells or both B cells and T cells, comprising administering a combination of an effective amount of an isolated binding molecule that specifically binds to Semaphorin-4D (SEMA4D) if the subject's B cell, T cell or both B cell and T cell levels are above a predetermined threshold level of B cells, T cells or both B cells and T cells, or are elevated relative to the level of B cells, T cells or both B cells and T cells, in one or more control samples that can include, but are not limited to, samples from other patients having atherosclerosis or from healthy, non-atherosclerotic patients. B cell, T cell, or B cell and T cell levels can be measured by a healthcare provider or by a clinical laboratory, where a sample, e.g., a blood sample, is obtained from the patient either by the healthcare provider or by the clinical laboratory. In one aspect, the patient's level of B cells, T cells or both B cells and T cells, can be measured in a cytometric-based immunophenotypic assay.

In certain embodiments, this disclosure also provides a method of treating a subject, e.g., a patient having atherosclerosis, comprising administering to the subject an effective amount of an isolated binding molecule that specifically binds to Semaphorin-4D (SEMA4D) if C-reactive protein (CRP) and/or low density lipoprotein (LDL) levels in a sample taken from the subject is above predetermined threshold levels, or is elevated relative to the CRP and/or LDL levels in one or more control samples. CRP and/or LDL levels expression in the subject can be measured by a healthcare provider or by a clinical laboratory. In certain aspects, CRP and/or LDL levels can be measured in situ, e.g., via imaging techniques. In certain aspects CRP and/or LDL levels expression can be measured in a sample obtained from the subject. In one aspect, CRP and/or LDL levels can be measured in an immunoassay employing antibodies or antigen binding fragments thereof which recognize CRP and/or LDL. In another aspect CRP and/or LDL levels can be measured via a quantitative gene expression assay, e.g., an RT-PCR assay.

This disclosure also provides methods, assays, and kits to facilitate a determination by a healthcare provider, a healthcare benefits provider, or a clinical laboratory to as to whether a subject, e.g., a patient having atherosclerosis or inflammatory disease, will benefit from treatment with either: (1) an effective amount of an isolated binding molecule that specifically binds to Semaphorin-4D (SEMA4D); or (2) an effective amount of an isolated binding molecule that specifically binds to Semaphorin-4D (SEMA4D), where the subject has, or is suspected to have, atherosclerosis or inflammatory disease. The methods, assays, and kits provided herein will also facilitate a determination by a healthcare provider, a healthcare benefits provider, or a clinical laboratory to as to whether a subject, e.g., a patient having atherosclerosis or inflammatory disease, will benefit from treatment with (1) an effective amount of an isolated binding molecule that specifically binds to Semaphorin-4D (SEMA4D) and an effective amount of at least one other immune modulating therapy; or (2) an effective amount of an isolated binding molecule that specifically binds to Semaphorin-4D (SEMA4D).

The present disclosure provides a method of treating a subject, e.g., a patient having atherosclerosis, comprising administering an effective amount of an isolated binding molecule that specifically binds to Semaphorin-4D (SEMA4D); if the level of B-cells, T-cells, or T-cells and B-cells in a sample taken from the patient is above a predetermined threshold level, or is above the level of B-cells, T-cells, or T-cells and B-cells in one or more control samples. In some aspects, the sample is obtained from the patient and is submitted for measurement of the level of B-cells, T-cells, or T-cells and B-cells in the sample, for example, to a clinical laboratory.

The present disclosure also provides a method of treating a subject determined to have atherosclerotic plaques, e.g., a patient having atherosclerosis, comprising administering an effective amount of an isolated binding molecule that specifically binds to Semaphorin-4D (SEMA4D). In certain embodiments, the subject is determined to have atherosclerotic plaques and is treated if the number, size, or characteristics of atherosclerotic plaques in the patient is above a predetermined threshold number, size, or character, or if the number, size, or character of atherosclerotic plaques in the subject is indicative of atherosclerosis when compared to one or more control samples. In some aspects, the sample is obtained from the patient and is submitted for measurement of the level of CRP and/or LDL in the sample, for example, to a clinical laboratory. In other aspects, the patient is subjected to an imaging technique to determine the number, size, or character of atherosclerotic plaques. Images that can be used in such methods include, but are not limited to, images obtained by coronary angiography, intravascular ultrasound (IVUS), carotid ultrasound, coronary computed tomography (CT), magnetic resonance imaging (MRI), positron emission tomography (PET), optical coherence tomography (OCT), near-infrared spectroscopy (NIRS), and NIR fluorescence. In certain embodiments, imaging techniques that have been described in the literature can be used (Tardif et al. Circ Cardiovasc Imaging. 2011; 4:319-333). In certain embodiments, treatment is administered if the atherosclerotic plaques are "vulnerable atherosclerotic plaques" having characteristics that include, but are not limited to, large lipid cores, low SMC content, high macrophage content, and a thin fibrous cap. The presence of "vulnerable atherosclerotic plaques" in a subject can be determined by a scoring system (Virmani et al. *Arterioscler Thromb Vasc Biol* 20(5): 1262-75 (2000)) or other techniques (van Lammeren et al., *Current Cardiology Reviews* 7:22-27 (2011)). In certain embodiments, subjects determined to have such "vulnerable atherosclerotic plaques" are treated according to the methods provided herein.

Also provided is a method of treating a subject, e.g., a patient having atherosclerosis, comprising (a) submitting a sample taken from the subject for measurement of the level of B-cells, T-cells, or T-cells and B-cells, or for measurement of CRP and/or LDL, in the sample; and, (b) administering an effective amount of an isolated binding molecule that specifically binds to Semaphorin-4D (SEMA4D) to the subject if the subject's level of B-cells, T-cells, or T-cells and B-cells, or the subject's level of CRP and/or LDL, is above a predetermined threshold level, or is above the level of B-cells, T-cells, or T-cells and B-cells, or the level of CRP and/or LDL, in one or more control samples.

The disclosure also provides a method of treating a subject, e.g., a patient having atherosclerosis, comprising (a) measuring the level of B-cells, T-cells, or T-cells and B-cells in a sample obtained from a subject, e.g., a patient having atherosclerosis, wherein the subject's level of B-cells, T-cells, or T-cells and B-cells in the sample is measured, e.g., in a cytometric-based immunophenotypic assay; (b) determining whether the level of B-cells, T-cells, or T-cells and B-cells in the sample is above a predetermined threshold level, or is above the level of B-cells, T-cells, or T-cells and B-cells in one or more control samples; and, (c) advising, instructing, or authorizing a healthcare provider to administer an effective amount of an isolated binding molecule that specifically binds to Semaphorin-4D (SEMA4D) to the subject if the subject's level of B-cells, T-cells, or T-cells and B-cells is above a predetermined threshold level, or is above the level of B-cells, T-cells, or T-cells and B-cells in one or more control samples.

In some aspects, the subject's level of B-cells, T-cells, or T-cells and B-cells can be measured in a cytometric-based immunophenotypic assay. In certain aspects, the assay can be performed on a sample obtained from the subject, by the healthcare professional treating the patient, e.g., using an assay as described herein, formulated as a "point of care" diagnostic kit. In some aspects, a sample can be obtained from the subject and can be submitted, e.g., to a clinical laboratory, for measurement of the level of B-cells, T-cells, or T-cells and B-cells in the sample according to the healthcare professional's instructions, including but not limited to, using a cytometric-based immunophenotypic assay as described herein. In certain aspects, the clinical laboratory performing the assay can advise the healthcare provider or a healthcare benefits provider as to whether the subject can benefit from treatment with an effective amount of an isolated binding molecule that specifically binds to Semaphorin-4D (SEMA4D), if the subject's level of B-cells, T-cells, or T-cells and B-cells is above a predetermined threshold level, or is above the level of B-cells, T-cells, or T-cells and B-cells in one or more control samples.

In certain aspects, results of an immunoassay, other diagnostic assay, and/or imaging can be submitted to a healthcare benefits provider for determination of whether the patient's insurance will cover treatment with an isolated binding molecule which specifically binds to Semaphorin-4D (SEMA4D).

VIII. Pharmaceutical Compositions and Administration Methods

Methods of preparing and administering anti-SEMA4D binding molecules, e.g., antibodies, or antigen-binding fragments, variants, or derivatives thereof to a subject in need thereof are well known to or are readily determined by those skilled in the art. The route of administration of the anti-SEMA4D binding molecule, e.g, antibody, or antigen-binding fragment, variant, or derivative thereof, can be, for example, oral, parenteral, by inhalation or topical. The term parenteral as used herein includes, e.g., intravenous, intraarterial, intraperitoneal, intramuscular, subcutaneous, rectal, or vaginal administration. While all these forms of administration are clearly contemplated as being within the scope of the invention, an example of a form for administration would be a solution for injection, in particular for intravenous or intraarterial injection or drip. A suitable pharmaceutical composition for injection can comprise a buffer (e.g. acetate, phosphate or citrate buffer), a surfactant (e.g. polysorbate), optionally a stabilizer agent (e.g. human albumin), etc. However, in other methods compatible with the teachings herein, anti-SEMA4D binding molecules, e.g., antibodies, or antigen-binding fragments, variants, or derivatives thereof can be delivered directly to the site of the adverse cellular population thereby increasing the exposure of the diseased tissue to the therapeutic agent.

As discussed herein, anti-SEMA4D binding molecules, e.g., antibodies, or antigen-binding fragments, variants, or derivatives thereof can be administered in a pharmaceutically effective amount for the in vivo treatment of inflammatory disorders. In this regard, it will be appreciated that the disclosed binding molecules can be formulated so as to facilitate administration and promote stability of the active agent. In certain embodiments, pharmaceutical compositions in accordance with the present invention comprise a pharmaceutically acceptable, non-toxic, sterile carrier such as physiological saline, non-toxic buffers, preservatives and the like. For the purposes of the instant application, a pharmaceutically effective amount of an anti-SEMA4D binding molecule, e.g., an antibody, or antigen-binding fragment, variant, or derivative thereof, shall be held to mean an amount sufficient to achieve effective binding to a target and to achieve a benefit, e.g., to reduce, inhibit, suppress and/or delay plaque formation or growth in a patient with atherosclerosis.

The pharmaceutical compositions used in this invention comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include, e.g., water, alcoholic/aqueous solutions, emulsions or suspensions, including saline and buffered media. In the subject invention, pharmaceutically acceptable carriers include, but are not limited to, 0.01-0.1 M, for example, 0.05 M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives can also be present such as, for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and in some aspects can be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Suitable formulations for use in the therapeutic methods disclosed herein are described in Remington's Pharmaceutical Sciences (Mack Publishing Co.) 16th ed. (1980).

Prevention of the action of microorganisms can be achieved by various antibacterial and antifungal agents, for example, parabens, chlorobutanol, phenol, ascorbic acid, thimerosal and the like. In certain aspects, pharmaceutical compositions can include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., an anti-SEMA4D antibody, or antigen-binding fragment, variant, or derivative thereof, by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, in some aspects, the methods of preparation include vacuum drying and freeze-drying, which yield a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations can be packaged and sold in the form of a kit. Such articles of manufacture can have labels or package inserts indicating that the associated compositions are useful for treating a subject suffering from, or predisposed to a disease or disorder.

Parenteral formulations can be a single bolus dose, an infusion or a loading bolus dose followed with a maintenance dose. These compositions can be administered at specific fixed or variable intervals, e.g., once a day, or on an "as needed" basis.

Certain pharmaceutical compositions used in this invention can be orally administered in an acceptable dosage form including, e.g., capsules, tablets, aqueous suspensions or solutions. Certain pharmaceutical compositions also can be administered by nasal aerosol or inhalation. Such compositions can be prepared as solutions in saline, employing benzyl alcohol or other suitable preservatives, absorption promoters to enhance bioavailability, and/or other conventional solubilizing or dispersing agents.

The amount of an anti-SEMA4D binding molecule, e.g., antibody, or fragment, variant, or derivative thereof, to be combined with the carrier materials to produce a single dosage form will vary depending upon the host treated and the particular mode of administration. The composition can be administered as a single dose, multiple doses or over an established period of time in an infusion. Dosage regimens also can be adjusted to provide the optimum desired response (e.g., a therapeutic or prophylactic response).

In keeping with the scope of the present disclosure, anti-SEMA4D antibodies, or antigen-binding fragments, variants, or derivatives thereof can be administered to a human or other animal in accordance with the aforementioned methods of treatment in an amount sufficient to produce a therapeutic effect. The anti-SEMA4D antibodies, or antigen-binding fragments, variants or derivatives thereof can be administered to such human or other animal in a conventional dosage form prepared by combining the antibody of the invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of anti-SEMA4D binding molecules, e.g., antibodies, or antigen-binding fragments, variants, or derivatives thereof, of the invention can be used.

By "therapeutically effective dose or amount" or "effective amount" is intended an amount of anti-SEMA4D binding molecule, e.g., antibody or antigen binding fragment, variant, or derivative thereof, that when administered brings about a positive therapeutic response with respect to treatment of a patient with a disease to be treated, e.g., a delay in the formation of atherosclerotic plaques; reduce, retard or stop an increase in new atherosclerotic plaque formation; inhibit, e.g., suppress, retard, prevent, stop, or reverse neovascularization in atherosclerotic plaques; change in the morphology or function of atherosclerotic plaques; or relieve to some extent one or more of the symptoms associated with atherosclerosis; reduce morbidity and mortality; improve quality of life; or a combination of such effects.

Therapeutically effective doses of the compositions of the present invention, e.g., to reduce, inhibit, suppress and/or delay atherosclerotic plaques, vary depending upon many different factors, including means of administration, target site, physiological state of the patient, whether the patient is human or an animal, other medications administered, and whether treatment is prophylactic or therapeutic. In certain embodiments the patient is a human, but non-human mammals including transgenic mammals can also be treated. Treatment dosages can be titrated using routine methods known to those of skill in the art to optimize safety and efficacy.

The amount of at least one anti-SEMA4D binding molecule, e.g., antibody or binding fragment, variant, or derivative thereof, to be administered is readily determined by one of ordinary skill in the art without undue experimentation given the disclosure of the present invention. Factors influencing the mode of administration and the respective amount of at least one anti-SEMA4D binding molecule, e.g., antibody, antigen-binding fragment, variant or derivative thereof include, but are not limited to, the severity of the disease, the history of the disease, and the age, height, weight, health, and physical condition of the individual undergoing therapy. Similarly, the amount of anti-SEMA4D binding molecule, e.g., antibody, or fragment, variant, or derivative thereof, to be administered will be dependent upon the mode of administration and whether the subject will undergo a single dose or multiple doses of this agent.

The invention also provides for the use of an anti-SEMA4D binding molecule, e.g., antibody of the invention, or antigen-binding fragment, variant, or derivative thereof, in the manufacture of a medicament for treating a subject with an inflammatory disorder, wherein the medicament is used in a subject that has been pretreated with at least one other therapy. By "pretreated" or "pretreatment" is intended the subject has received one or more other therapies (e.g., been treated with at least one other inflammatory therapy) prior to receiving the medicament comprising the anti-SEMA4D binding molecule, e.g., antibody or antigen-binding fragment, variant, or derivative thereof. "Pretreated" or "pretreatment" includes subjects that have been treated with at least one other therapy within 2 years, within 18 months, within 1 year, within 6 months, within 2 months, within 6 weeks, within 1 month, within 4 weeks, within 3 weeks, within 2 weeks, within 1 week, within 6 days, within 5 days, within 4 days, within 3 days, within 2 days, or even within 1 day prior to initiation of treatment with the medicament comprising the anti-SEMA4D binding molecule, for example, the monoclonal antibody VX15/2503 disclosed herein, or antigen-binding fragment, variant, or derivative thereof. It is not necessary that the subject was a responder to pretreatment with the prior therapy or therapies. Thus, the subject that receives the medicament comprising the anti-SEMA4D binding molecule, e.g., an antibody or antigen-binding fragment, variant, or derivative thereof could have responded, or could have failed to respond, to pretreatment with the prior therapy, or to one or more of the prior therapies where pretreatment comprised multiple therapies.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular Immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described are generally followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (W.H. Freeman and Co., NY).

Standard reference works setting forth general principles of immunology include Current Protocols in Immunology, John Wiley & Sons, New York; Klein (1982) J., Immunology: The Science of Self-Nonself Discrimination (John Wiley & Sons, NY); Kennett et al., eds. (1980) Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevier, Amsterdam); Goldsby et al., eds. (2000) Kuby Immunology (4th ed.; H. Freemand & Co.); Roitt et al. (2001) Immunology (6th ed.; London: Mosby); Abbas et al. (2005) Cellular and Molecular Immunology (5th ed.; Elsevier Health Sciences Division); Kontermann and Dubel (2001) Antibody Engineering (Springer Verlag); Sambrook and Russell (2001) Molecular Cloning: A Laboratory Manual (Cold Spring Harbor Press); Lewin (2003) Genes VIII (Prentice Hall 2003); Harlow and Lane (1988) Antibodies: A Laboratory Manual (Cold Spring Harbor Press); Dieffenbach and Dveksler (2003) PCR Primer (Cold Spring Harbor Press).

All of the references cited above, as well as all references cited herein, are incorporated herein by reference in their entireties.

The following examples are offered by way of illustration and not by way of limitation.

EXAMPLES

Example 1

Testing the Ability of an Anti-SEMA4D Binding Molecule, e.g., an Antibody or Antigen-Binding Fragment, Variant, or Derivative Thereof, e.g., VX15/2503, to Inhibit Atherosclerotic Plaque Formation and Reduce Neovascularization in Spontaneously Hyperlipidemic (SHL) Mice with ApoE-Deficiency Experimental Design.

The following experiment examined whether treatment with anti-Sema4D blocking antibody of atherosclerosis-prone spontaneously hyperlipidemic (SHL) mice with ApoE-deficiency could reduce plaque growth and neovascularization.

Mice.

Male spontaneously hyperlipidemic (SHL) mice with apolipoprotein E (ApoE) deficiency under a genetic background of C57BL/6, C57BL/6.KOR/Stm Slc-Apoe$^{sh1}$ were obtained from Japan SLC, Inc. (Shizuoka, Japan). The SHL mice were fed a normal diet and housed in the animal center in the faculty of Pharmacy, Meijo University. All experimental protocols were approved by the institutional Animal Ethics Review Committee.

Antibody Treatment of Mice.

Male 14-week-old SHL mice were randomly assigned into two groups and each group was administered either mouse control monoclonal antibody (n=10) (Control Ab 2B8.1E7, Vaccinex, Inc., Rochester, N.Y.) or mouse anti-SEMA4D neutralizing monoclonal antibody (n=9) (VX15/67-2, Vaccinex, Inc.) at 0.6 mg per mouse by intraperitoneal injection once a week. After 12 weeks of treatment, mice were sacrificed.

Tissue Processing.

The mouse aorta was perfused for 3 min through a 21 gauge needle inserted into the left ventricular apex using phosphate-buffered saline (PBS) and then for another 3 min with 4% buffered paraformaldehyde (pH 7.4). The aortic arch with its main branch points (branchiocephalic trunk, left common carotid artery and left subclavian artery) as well as the thoracic and abdominal aorta were excised and fixed in 4% buffered paraformaldehyde (pH 7.4). The aorta was then stained with Sudan IV (Sigma-Aldrich, St. Louis, Mo.) to reveal sudanophilic lipid deposits and the percentage of lipid plaque area to total aortic area was quantified using Image J Software (Wayne Rasband, NIH, Bethesda, Md.) following the literature (Dougherty A et al., *Methods in Molecular Biology*, vol. 209: Transgenic Mouse Methods and Protocols. Humana Press Inc., Totowa, N.J., pp. 293-309, 2002).

Immunohistochemistry and Morphometry.

The aortic arch excised from anesthetized mice was fixed in 4% buffered paraformaldehyde (pH 7.4). All vessels were embedded longitudinally in paraffin and cut into 1-μm serial sections. Sections were immunolabeled with anti-mouse CD31 antibody (BD, Franklin Lakes, N.J.) to stain endothelial cells. They were subsequently incubated with dextran polymer conjugated with secondary antibodies and peroxidase (DakoCytomation, Kyoto, Japan). To detect neovascularization, the sections were pretreated with 10 μg/ml proteinase K (Life technologies Japan, Tokyo, Japan) for 15 min at room temperature and incubated for 1 h at room temperature with 7.5 mg/ml isolectin B4 from *Bandeiraea simpilicifolia* conjugated with fluorescein (Sigma-Aldrich). Isolectin B4 (IB4) binds to terminal α-galactosyl residues expressed by endothelial cells. The degree of neovascularization was determined as a percentage calculated by dividing the isolectin B4 or CD31-positive area by the respective plaque area using the Image-J morphometry system (Wayne Rasband).

Statistical Analysis.

Data were expressed as means±S.E. Anti-Sema4D antibody-treated SHL mice were compared with control antibody-treated SHL mice using Student's t-test. Data were statistically significant at * $p<0.05$, ** $p<0.01$.

Anti-Sema4D Antibody Treatment Inhibited Development of Atherosclerotic Plaques.

To analyze the effect of anti-Sema4D antibody treatment in SHL mice with ApoE-deficiency on atherosclerosis development, aortas dissected from both control antibody-treated and anti-Sema4D antibody-treated SHL mice underwent sudanophilic staining of lipid deposits. FIG. 1A shows a significant inhibition of atherosclerotic plaque development in aortic regions of anti-Sema4D antibody-treated SHL mice when compared with control antibody-treated group. As shown in FIG. 1A, a quantitative measurement of the atherosclerotic plaque areas shows that the mean percentage of sudanophilic areas relative to the whole aortic region in anti-Sema4D antibody-treated SHL mice was significantly smaller than that in control antibody-treated group (anti-Sema4D antibody-treated mice: 4.89±1.11% vs. control antibody-treated mice: 17.64±3.41%; p=0.002). These findings demonstrate that using an anti-SEMA4D antibody to block Sema4D activity during the progression phase of atherosclerosis decreases plaque growth.

Less Neovascularization in the Atherosclerotic Plaques of Anti-Sema4D Antibody-Treated SHL Mice.

To study new vessel formation in the atherosclerotic plaques, isolectin B4 staining was employed to detect neovascularization in both control antibody-treated SHL plaques and anti-Sema4D antibody-treated SHL plaques. The results revealed that the percentage of isolectin B4 positive staining in the anti-Sema4D antibody-treated plaques was significantly less than in the control antibody-treated SHL plaques (anti-Sema4D antibody-treated SHL mice: 0.35±0.04% vs. control antibody-treated SHL mice: 1.70±0.24%; P<0.001, FIG. 1B).

Immunohistochemistry using antibodies against CD31, a marker for endothelial cells, also showed that CD31 positive areas were significantly reduced in the anti-Sema4D antibody-treated SHL plaques compared with control antibody-treated SHL plaques (anti-Sema4D antibody-treated SHL mice: 12.62±1.34% vs. control antibody-treated SHL mice: 19.30±1.22%; P=0.012, FIG. 1C), underscoring poor neovascularization in anti-Sema4D antibody-treated SHL mice plaques.

These findings demonstrate that blocking Sema4D activity during the progression phase of atherosclerosis acts to decrease neovascularization. Moreover, they demonstrate that anti-SEMA4D antibody blocks the migration of endothelial progenitor cells into the atherosclerotic plaque, which, in turn, leads to the decrease of both plaque neovascularization and plaque growth.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims and list of embodiments disclosed herein. Although specific terms are employed herein, they are used in a generic and descriptive sense only and not for purposes of limitation.

What is claimed is:

1. A method for inhibiting, suppressing, reducing or delaying growth of atherosclerotic plaques in a subject, comprising administering to a subject in need thereof an effective amount of an isolated antibody or antigen-binding fragment thereof that specifically binds to Semaphorin-4D (SEMA4D).

2. The method of claim 1, wherein the antibody or antigen-binding fragment thereof inhibits SEMA4D interaction with its receptor.

3. The method of claim 2, wherein the receptor is Plexin-B1, Plexin-B2, or CD72.

4. The method of claim 1, wherein the antibody or antigen-binding fragment thereof inhibits SEMA4D-mediated Plexin-B1 signal transduction.

5. The method of claim 1, wherein the subject has cardiovascular disease.

6. The method of claim 5, wherein the cardiovascular disease is selected from the group consisting of coronary heart disease, ischemic heart disease, coronary artery disease, cardiomyopathy, hypertensive heart disease, heart failure, cor pulmonale, cardiac dysrhythmias, inflammatory heart disease endocarditis, inflammatory cardiomegaly, myocarditis, valvular heart disease, cerebrovascular disease, peripheral arterial disease, congenital heart disease, rheumatic heart disease, and a combination thereof.

7. The method of claim 1, wherein the isolated antibody or antigen-binding fragment thereof specifically binds to the same SEMA4D epitope as a reference monoclonal antibody VX15/2503 or 67.

8. The method of claim 1, wherein the isolated antibody or antigen-binding fragment thereof competitively inhibits a reference monoclonal antibody VX15/2503 or 67 from specifically binding to SEMA4D.

9. The method of claim 1, wherein the antibody or antigen-binding fragment thereof comprises a variable heavy chain (VH) comprising VHCDRs 1-3 comprising SEQ ID NOs 6, 7, and 8, respectively, and a variable light chain (VL) comprising VLCDRs 1-3 comprising SEQ ID NOs 14, 15, and 16, respectively.

10. The method of claim 9, wherein the VH and VL comprise, respectively, SEQ ID NO: 9 and SEQ ID NO: 17 or SEQ ID NO: 10 and SEQ ID NO: 18.

11. The method of claim 1, wherein the method further includes inhibiting, reducing or delaying neovascularization around the atherosclerotic plaques.

12. A method for inhibiting, reducing or delaying neovascularization of atherosclerotic plaques in a subject, comprising administering to a subject in need thereof an effective amount of an isolated antibody or antigen-binding fragment thereof that specifically binds to Semaphorin-4D (SEMA4D).

13. The method of claim 12, wherein the antibody or antigen-binding fragment thereof inhibits SEMA4D interaction with its receptor.

14. The method of claim 13, wherein the receptor is Plexin-B1, Plexin-B2, or CD72.

15. The method of claim 12, wherein the antibody or antigen-binding fragment thereof inhibits SEMA4D-mediated Plexin-B1 signal transduction.

16. The method of claim 12, wherein the subject has cardiovascular disease.

17. The method of claim 16, wherein the cardiovascular disease is selected from the group consisting of coronary heart disease, ischemic heart disease, coronary artery disease, cardiomyopathy, hypertensive heart disease, heart failure, cor pulmonale, cardiac dysrhythmias, inflammatory heart disease endocarditis, inflammatory cardiomegaly, myocarditis, valvular heart disease, cerebrovascular disease, peripheral arterial disease, congenital heart disease, rheumatic heart disease, and a combination thereof.

18. The method of claim 12, wherein the isolated antibody or antigen-binding fragment thereof specifically binds to the same SEMA4D epitope as a reference monoclonal antibody VX15/2503 or 67.

19. The method of claim 12, wherein the isolated antibody or antigen-binding fragment thereof competitively inhibits a reference monoclonal antibody VX15/2503 or 67 from specifically binding to SEMA4D.

20. The method of claim 12, wherein the antibody or antigen-binding fragment thereof comprises a variable heavy chain (VH) comprising VHCDRs 1-3 comprising SEQ ID NOs 6, 7, and 8, respectively, and a variable light chain (VL) comprising VLCDRs 1-3 comprising SEQ ID NOs 14, 15, and 16, respectively.

21. The method of claim 20, wherein the VH and VL comprise, respectively, SEQ ID NO: 9 and SEQ ID NO: 17 or SEQ ID NO: 10 and SEQ ID NO: 18.

22. A method for treating a subject determined to have atherosclerotic plaques, comprising: administering to a subject determined to have atherosclerotic plaques an effective amount of an isolated antibody or antigen-binding fragment thereof that specifically binds to Semaphorin-4D (SEMA4D), thereby inhibiting, reducing or delaying growth of atherosclerotic plaques.

* * * * *